US012752112B2

(12) United States Patent
Urbin

(10) Patent No.: US 12,752,112 B2
(45) Date of Patent: Oct. 6, 2026

(54) DEVICES, SYSTEMS, AND METHODS FOR AURICULAR VAGUS NERVE STIMULATION

(71) Applicant: United States Government As Represented By The Department of Veterans Affairs, Washington, DC (US)

(72) Inventor: Michael A Urbin, Pittsburgh, PA (US)

(73) Assignee: UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 776 days.

(21) Appl. No.: 17/378,098

(22) Filed: Jul. 16, 2021

(65) Prior Publication Data

US 2022/0016425 A1 Jan. 20, 2022

Related U.S. Application Data

(60) Provisional application No. 63/053,271, filed on Jul. 17, 2020.

(51) Int. Cl.
*A61N 1/36* (2006.01)
*A61N 1/04* (2006.01)

(52) U.S. Cl.
CPC ....... *A61N 1/36036* (2017.08); *A61N 1/0456* (2013.01); *A61N 1/0484* (2013.01)

(58) Field of Classification Search
CPC .............. A61N 1/36036; A61N 1/0456; A61N 1/0484; A61N 1/0472; A61N 1/36053; A61N 1/36025; A61N 1/36034; A61N 1/36014; A61N 1/0492; A61N 2007/0026; A61N 1/0541; A61N 1/0534; A61N 1/36139; A61N 1/36185; A61N 1/0529;
(Continued)

(56) References Cited

U.S. PATENT DOCUMENTS

2005/0165460 A1 7/2005 Erfan
2007/0250145 A1 10/2007 Kraus et al.
(Continued)

FOREIGN PATENT DOCUMENTS

CN 105056394 B 5/2017
JP 2013-052179 A 3/2013
(Continued)

OTHER PUBLICATIONS

John L. Barbur Learning from the pupil—studies of basic mechanisms and clinical applications. In: L. M. Chalupa and J. S. Werner, Eds. The Visual Neurosciences. Cambridge, Mass.: MIT Press, 2004, vol. 1, pp. 641-656.
(Continued)

*Primary Examiner* — Benjamin J Klein
*Assistant Examiner* — Daniel Tehrani
(74) *Attorney, Agent, or Firm* — BALLARD SPAHR LLP

(57) ABSTRACT

A method of acutely activating the noradrenergic systems in a subject can comprise applying one or more electrical pulses to an ear canal (e.g., the left ear canal) of the subject, wherein the one or more electrical pulses are sufficient to acutely activate the noradrenergic system of the subject. Apparatuses and systems for applying one or more electrical pulses to an ear canal are also disclosed.

20 Claims, 26 Drawing Sheets

(58) Field of Classification Search
CPC .............. A61N 1/3605; A61N 1/36082; A61N 1/36135; A61N 1/3614; A61N 1/36067; A61N 1/36182; A61N 2001/083; A61N 1/0531; A61N 1/36125; A61N 1/372; A61B 5/4035; A61B 5/4836
See application file for complete search history.

(56) References Cited

U.S. PATENT DOCUMENTS

| | | | | |
|---|---|---|---|---|
| 2011/0029038 A1* | 2/2011 | Hyde | A61N 1/3611 607/45 |
| 2013/0245486 A1* | 9/2013 | Simon | A61B 5/4836 607/46 |
| 2014/0313488 A1* | 10/2014 | Kiderman | A61B 3/005 351/246 |
| 2015/0018926 A1 | 1/2015 | Frenkel | |
| 2015/0148878 A1* | 5/2015 | Yoo | A61N 1/0456 607/148 |
| 2016/0279021 A1* | 9/2016 | Hyde | A61H 23/0245 |
| 2017/0113042 A1* | 4/2017 | Goodall | A61N 5/0622 |
| 2018/0339148 A1 | 11/2018 | Kong | |
| 2019/0167095 A1* | 6/2019 | Krueger | A61B 3/113 |
| 2021/0000339 A1* | 1/2021 | Neice | A61B 3/0025 |

FOREIGN PATENT DOCUMENTS

| | | |
|---|---|---|
| WO | WO 2019-005774 A1 | 1/2019 |
| WO | WO 2019-028000 A1 | 2/2019 |

OTHER PUBLICATIONS

International Search Authority Search Report and Written Opinion for corresponding PCT Application No. PCT/US2021/042014, dated Nov. 29, 2021.

Supplementary European Search Report for corresponding EP Application No. EP 21 84 2043, dated May 3, 2024.

* cited by examiner

FIG. 5B
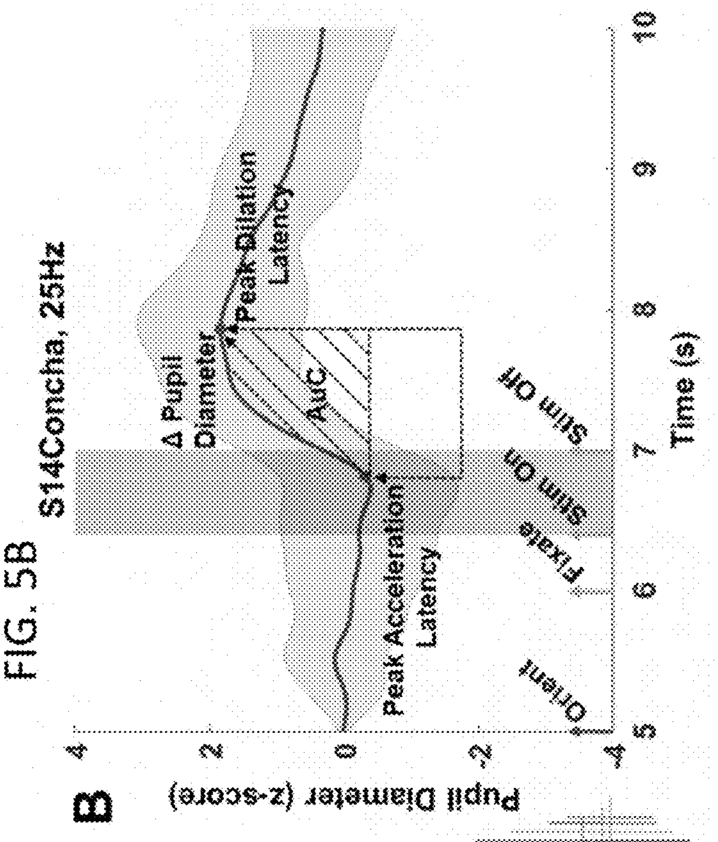
FIG. 5B
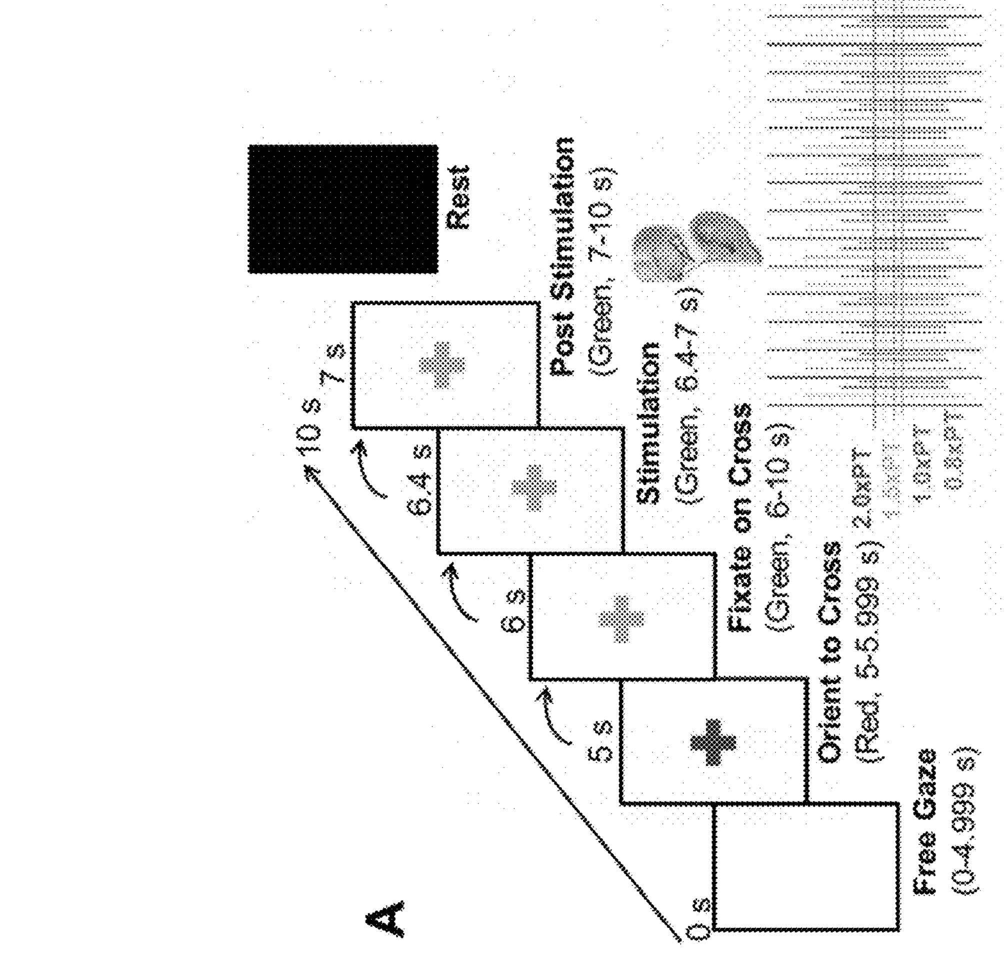
FIG. 5A

DEVICES, SYSTEMS, AND METHODS FOR AURICULAR VAGUS NERVE STIMULATION

CROSS-REFERENCE TO RELATED APPLICATIONS

This application claims priority to and the benefit of the filing date of U.S. Provisional Patent Application No. 63/053,271, filed Jul. 17, 2020, the entirety of which is hereby incorporated by reference herein.

STATEMENT REGARDING FEDERALLY SPONSORED RESEARCH

This invention was made with government support under Grant Number 51K2RX002837 awarded by the Department of Veterans Affairs. The government has certain rights in this invention.

BACKGROUND

Various diseases, such as certain psychiatric disorders, neurological disorders, chronic inflammatory disorders, or other disorders described further herein lack adequate treatment. Moreover, noninvasive treatments for such diseases are even more limited in availability or efficacy. Accordingly, a safe and effective treatment is desirable.

BRIEF SUMMARY

Disclosed are methods of acutely activating the noradrenergic system in a subject comprising applying one or more electrical pulses to an car of the subject, wherein the one or more electrical pulses are sufficient to acutely activate the noradrenergic system in the subject.

Disclosed are methods of treating a disease or disorder in a subject comprising applying one or more electrical pulses to an ear of the subject, wherein the one or more electrical pulses are sufficient to acutely activate the noradrenergic system in the subject such that the disease or disorder in the subject is treated.

Disclosed are methods of treating a subject in need thereof comprising applying one or more electrical pulses to an ear of the subject, wherein the one or more electrical pulses are sufficient to acutely activate the noradrenergic system of the subject in need thereof.

Disclosed are methods to support learning in a subject in need thereof comprising applying one or more electrical pulses to an ear of the subject, wherein the one or more electrical pulses are sufficient to acutely activate the noradrenergic system of the subject in need thereof, wherein the subject in need thereof has enhanced learning.

Disclosed is an apparatus comprising an elongate body having a longitudinal axis and a first end and a second end that are spaced along the longitudinal axis. A first electrode can be positioned at the first end of the elongate body. The first electrode can be configured to be received at least partially in an ear canal of an ear. A second electrode can be positioned between the first electrode and the second end of the elongate body. A first conductor can be in electrical communication with the first electrode, and a second conductor can be in electrical communication with the second electrode. A housing can receive a portion of the elongate body therein. The housing can have a central axis. The elongate body can be pivotable relative to the housing about the central axis. The housing can be configured to retain the elongate body in a plurality of positions that are offset from each other by at least an azimuthal angle offset. The apparatus can be configured to provide electrical stimulation through or between the first and second electrodes. The housing can comprise a support element that is configured to support the apparatus on an outer car portion of the car to permit electrical stimulation of a nerve (e.g., an auricular branch of the vagus nerve) adjacent to or within the ear.

A system can comprise the apparatus and a stimulation generator in communication with the first electrical conductor and the second electrical conductor. The stimulation generator can be configured to generate current for providing electrical stimulation through or between the first and second electrodes of the apparatus.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 1A shows the results from auditory fear conditioning of groups undergoing extinction training paired with sham stimulation or VNS or extended extinction. Note that extinction training paired with VNS accelerates extinction of the fear response. FIG. 1B shows the results from a PTSD model during extinction training paired with either sham stimulation or VNS. Note that the VNS group shows enhanced extinction of the fear response.

FIG. 3A shows the number of successful attempts at achieving target force and FIG. 3B shows the peak force achieved is greatest in the group that trained with VNS that temporally coincides with successful performance.

FIG. 5A and FIG. 5B are eye tracking studies. FIG. 5A shows timing of events during an eye tracking paradigm (left) with 25 Hz pulse trains applied at each multiplier of perceptual threshold (right). FIG. 5B shows representative recording of pupil diameter during eye tracking procedures. A pupillary response is shown with the various response features (i.e., size and timing) annotated. Gray vertical bar corresponds to the stimulation epoch.

FIG. 6A shows the acceleration-time profile of pupil diameter in two representative subjects when 25 Hz (gray) and 300 Hz (black) pulse frequencies are administered. FIG. 6B shows corresponding pupil diameter at each pulse frequency.

Circles indicate the time of peak positive acceleration, and the lighter shade vertical bar corresponds to the stimulation epoch. Note that the greatest rate of change in pupil diameter occurs at the time of peak acceleration.

Figure 7A:
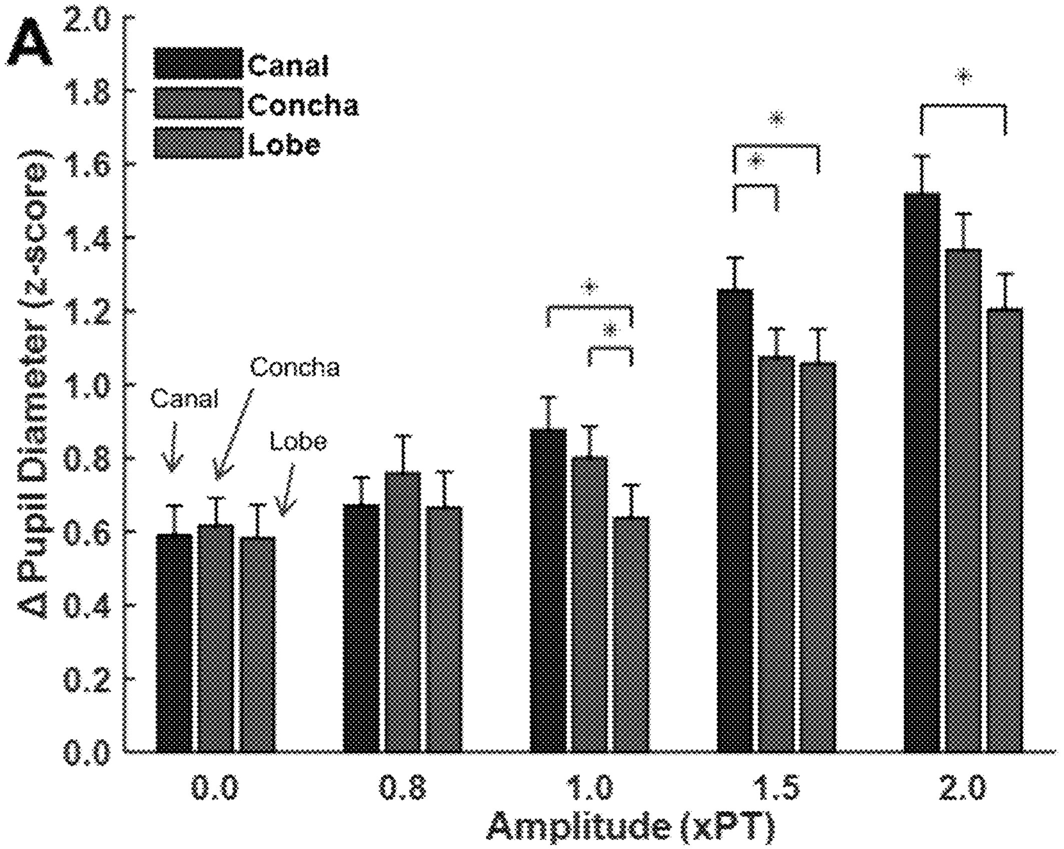
Figure 7B:
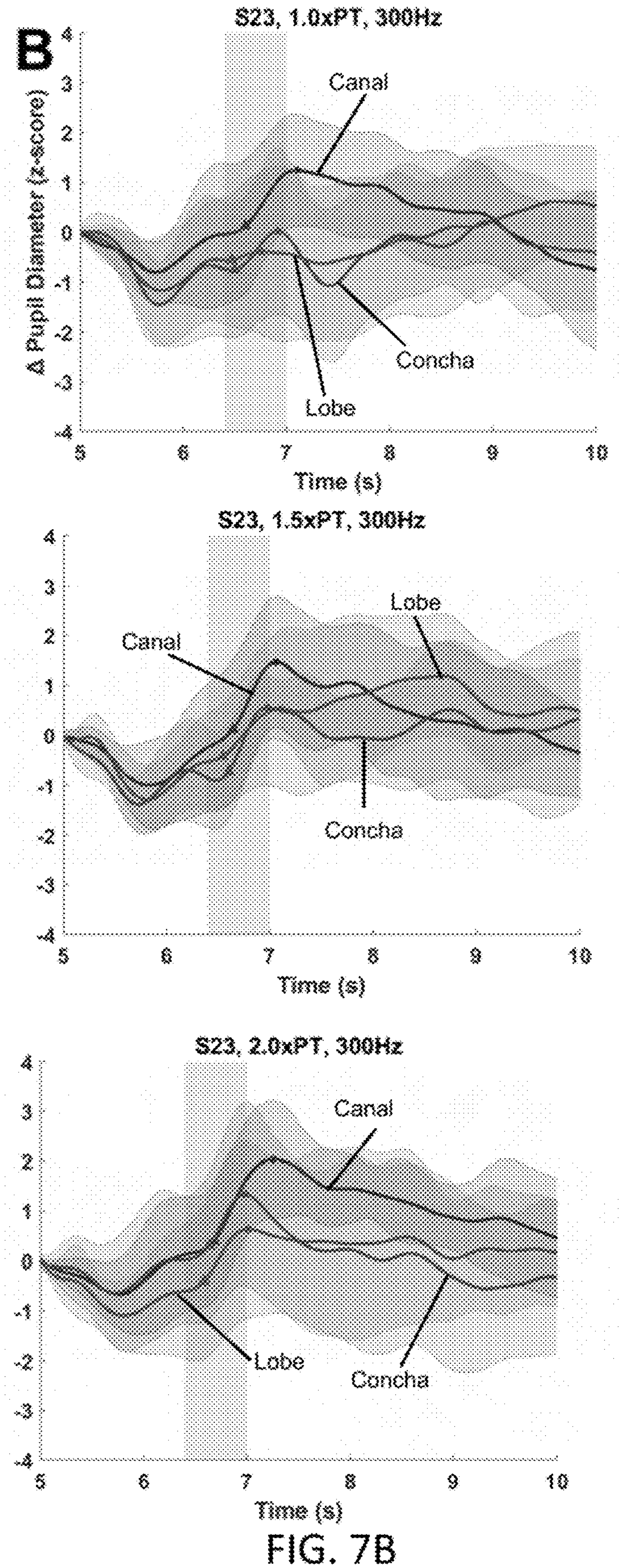

FIG. 7A and FIG. 7B are studies on pupil diameter. FIG. 7A shows the change in pupil diameter by location and pulse amplitude in a sample (n=19) of neurologically-intact humans (*p<0.05). Note the gradation by pulse amplitudes at and above perceptual threshold, particularly for the canal location. Error bars represent standard error of the mean. FIG. 7B shows waveform-averaged pupil diameter recordings from a representative subject when pulse trains were applied to different landmarks [i.e., canal, concha, and lobe] with pulse amplitudes at and above PT [i.e., 1.0×PT (left), 1.5×PT (middle), and 2.0×PT (right)]. Triangles and circles correspond to the time of peak positive acceleration and peak dilation, respectively. Gray vertical bar corresponds to the stimulation epoch.

Figure 8A:
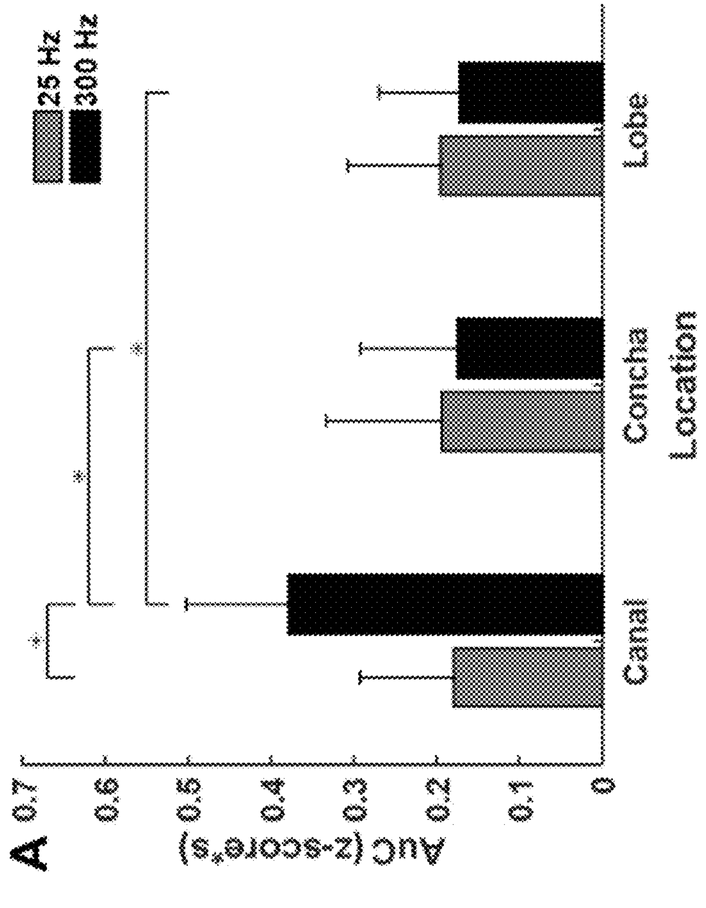
Figure 8B:
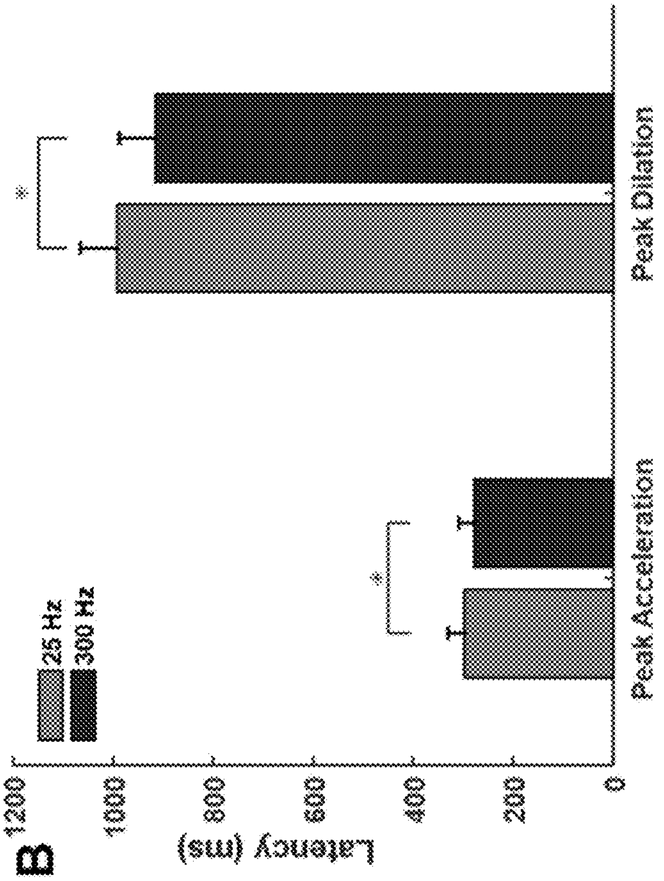

FIG. 8A and FIG. 8B are studies on pupil dilation. FIG. 8A shows area under the curve (AuC) of the pupillary response between the times of peak positive acceleration and peak dilation by location. AuC modulated with pulse frequency when pulse trains were applied to the canal location. 300 Hz pulse frequency produced pupillary responses with greater AuC when pulse trains were applied to the canal versus the concha and lobe (*p<0.05). FIG. 8B shows latencies of peak acceleration and dilation by pulse frequency. Higher pulse frequency reduced the latency of both events (*p<0.05). Error bars represent standard error of the mean.

Figures 9A, 9B:
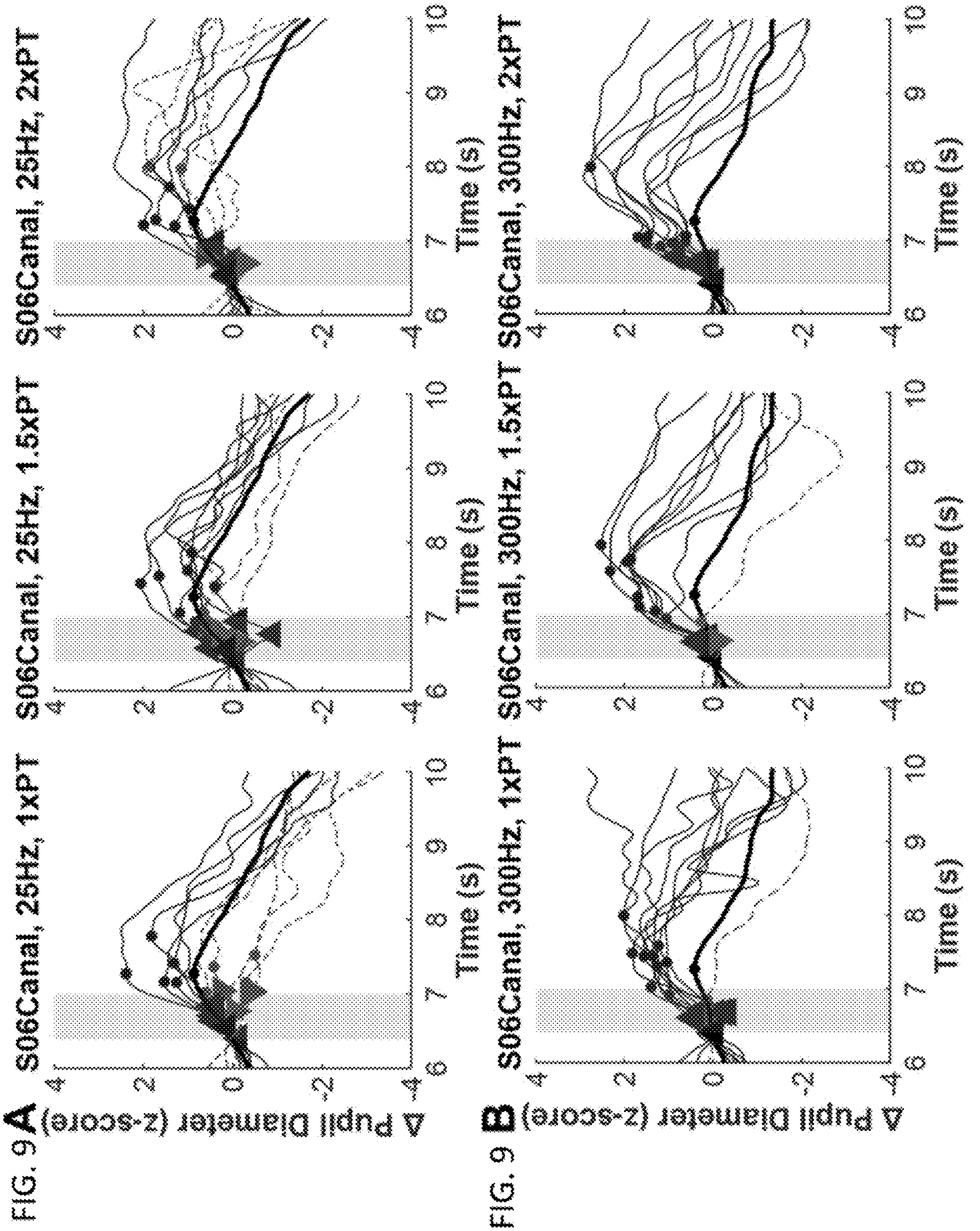

FIG. 9A and FIG. 9B show pupil diameter. FIG. 9A shows pupil diameter recordings while single, 25 Hz pulse trains were applied to the canal location with pulse amplitudes at and above perceptual threshold (i.e., 1.0×PT-2.0×PT, left to right). FIG. 9B shows pupil diameter recordings while single, 300 Hz pulse trains were applied to the canal location with pulse amplitudes at and above perceptual threshold (1.0×PT-2.0×PT, left to right). Thin-solid and broken traces correspond to instances where single pulse trains did or did not elicit pupillary responses, respectively. The bold trace corresponds to the waveform-averaged pupil diameter recording in the 0.0×PT amplitude condition that was randomized into each block of trials. Note that single pulse trains modulate the noradrenergic biomarker within the stimulation epoch, providing evidence of acute activation. Triangles correspond to the time of peak positive acceleration (inverted if pupillary response is not elicited), and circles correspond to peak dilation. Error bars represent standard error of the mean.

Figure 10:
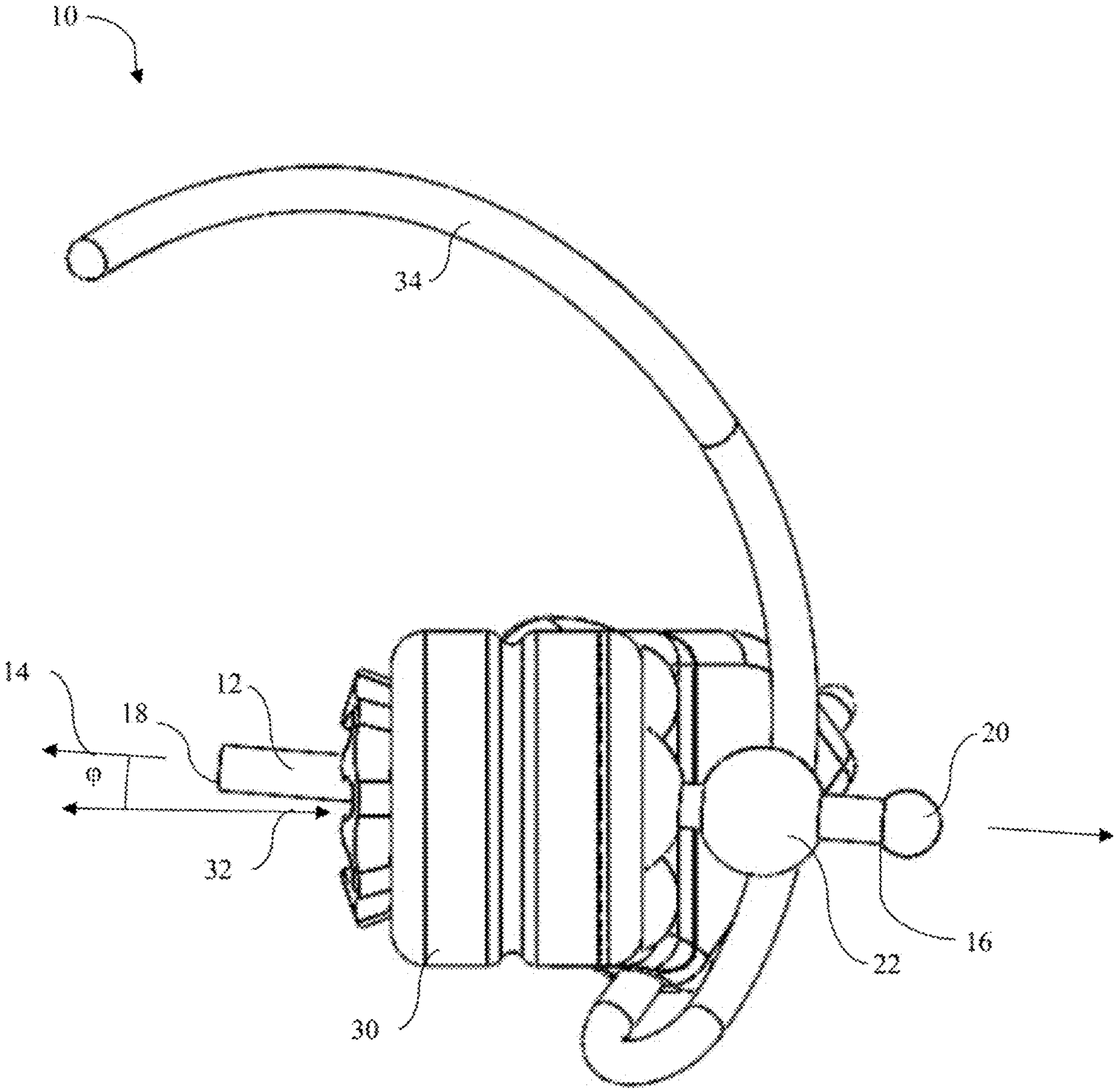

FIG. 10 is a front view of an apparatus for providing stimulation in accordance with embodiments disclosed herein.

Figure 11:
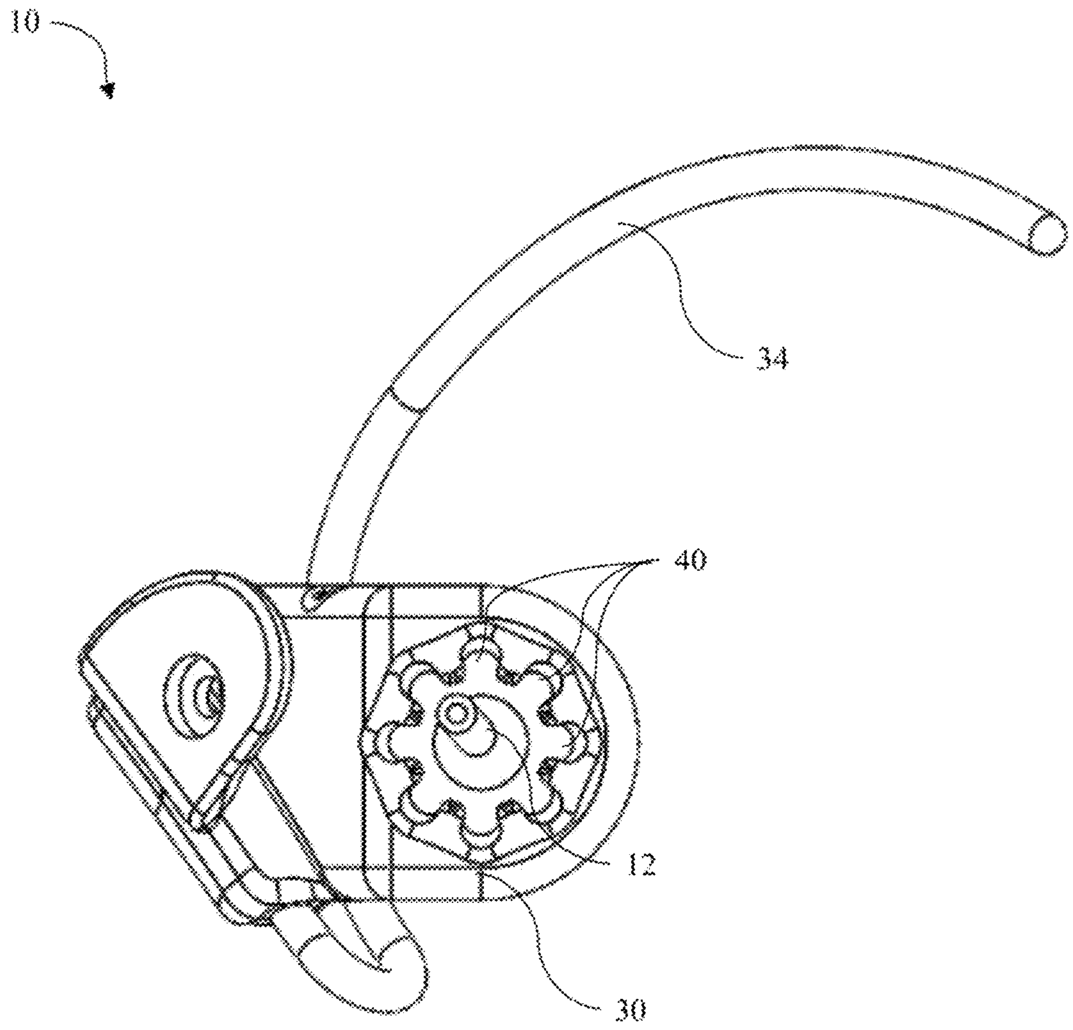

FIG. 11 is a side view of the apparatus of FIG. 10.

Figure 12:
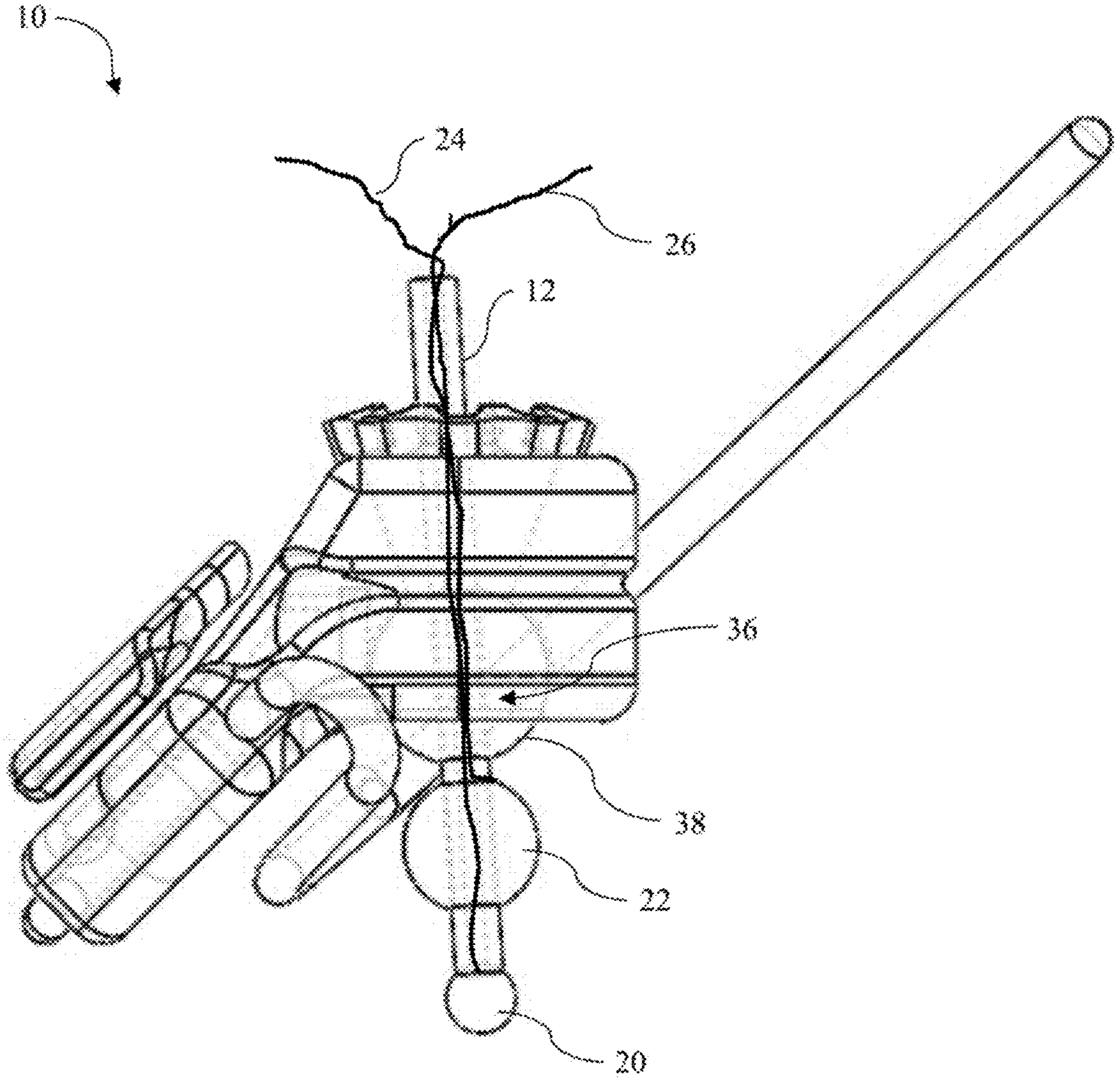

FIG. 12 is a top view of the apparatus of FIG. 10, showing hidden lines.

Figure 13:
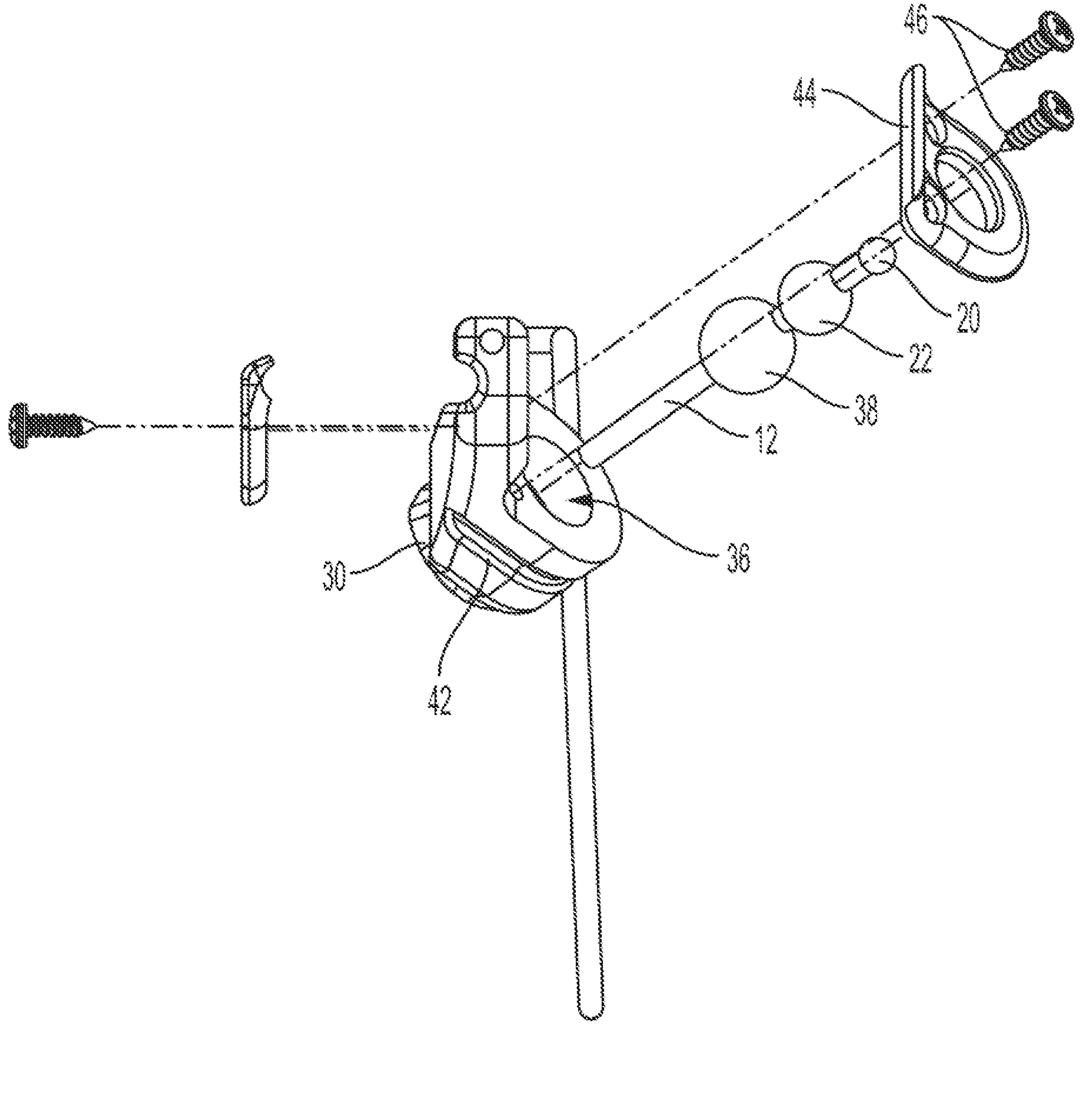

FIG. 13 is an exploded view of the apparatus of FIG. 10.

Figure 14:
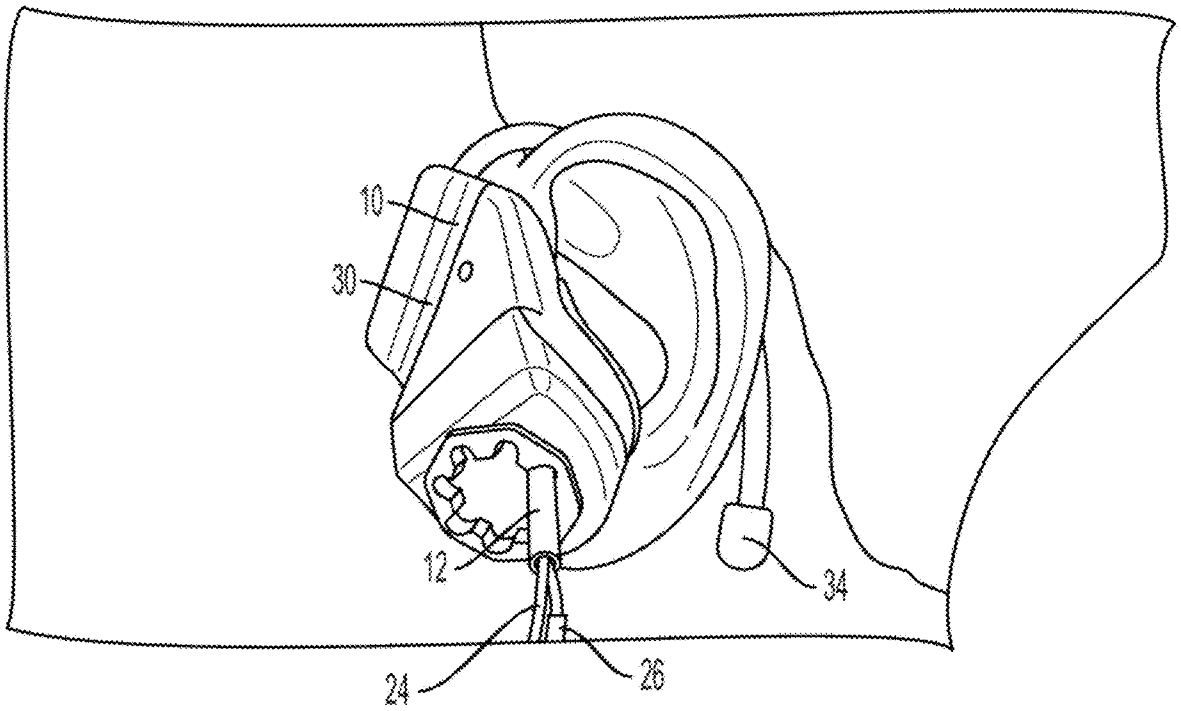

FIG. 14 is a side view of the apparatus being worn on an car of a user.

Figure 15:
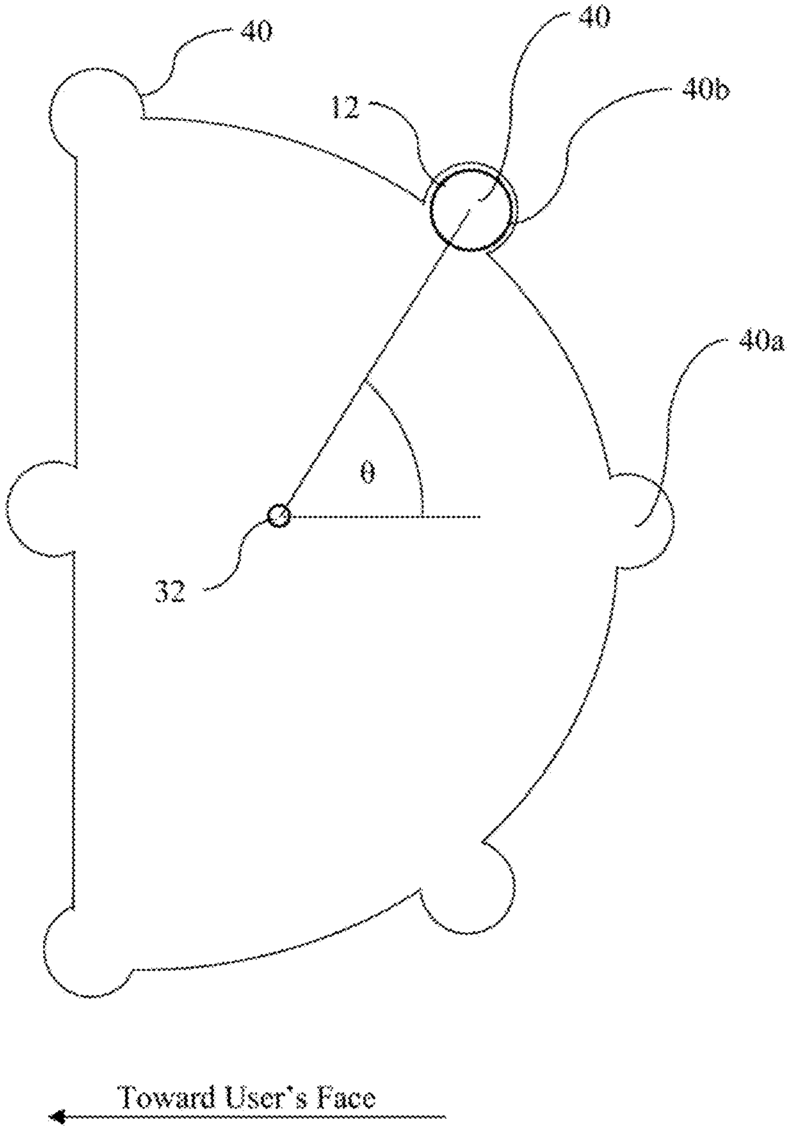

FIG. 15 is a schematic diagram of a plurality of detents of a housing of an apparatus for providing stimulation in accordance with embodiments disclosed herein.

Figure 16A:
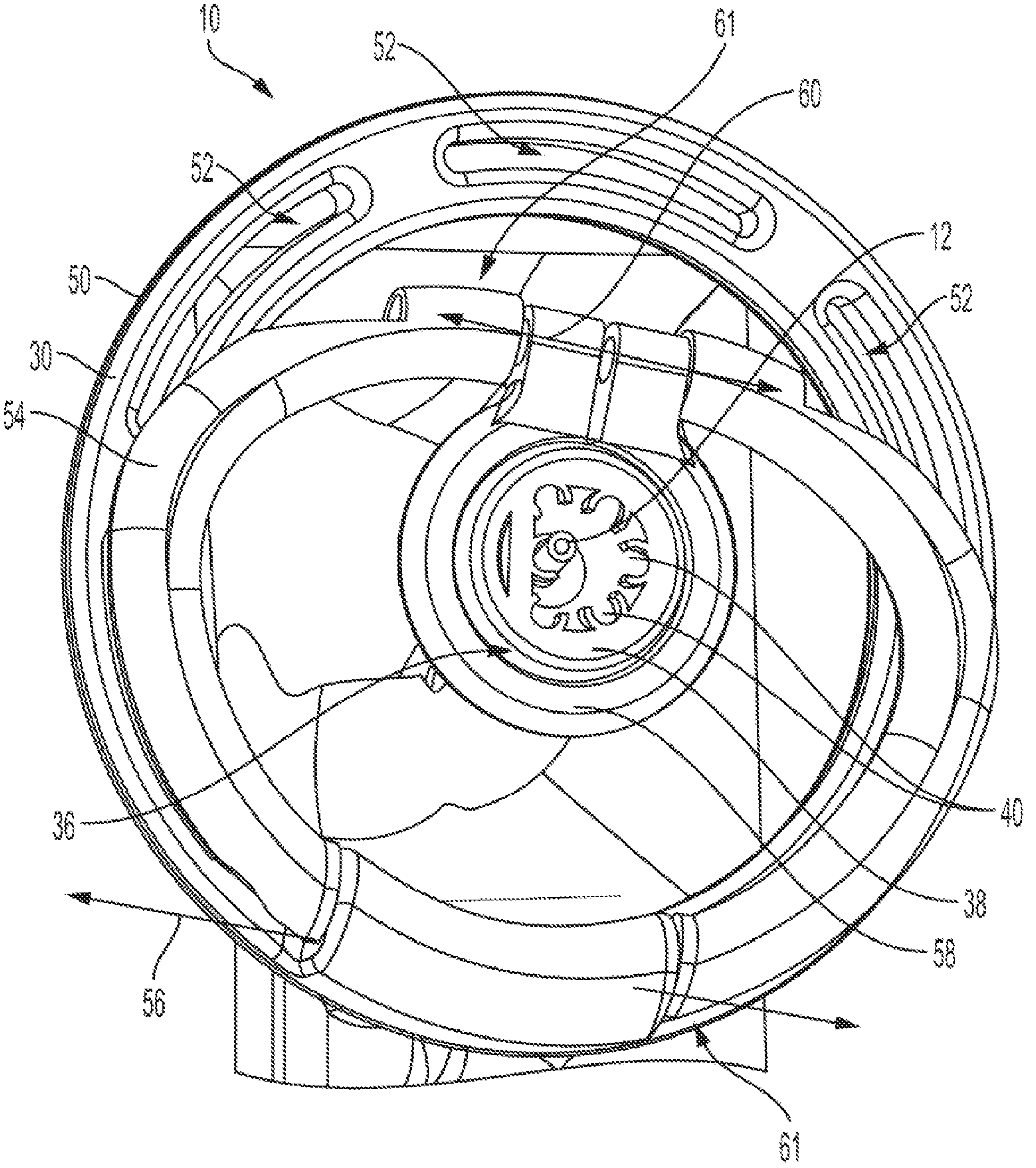
Figure 16B:
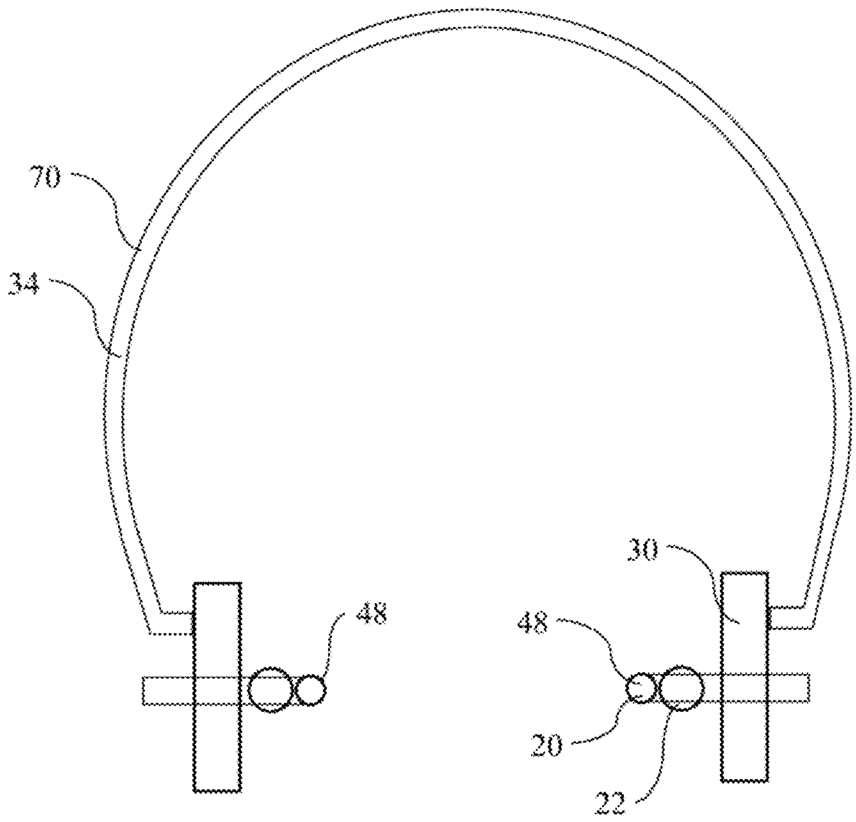
Figure 16C:
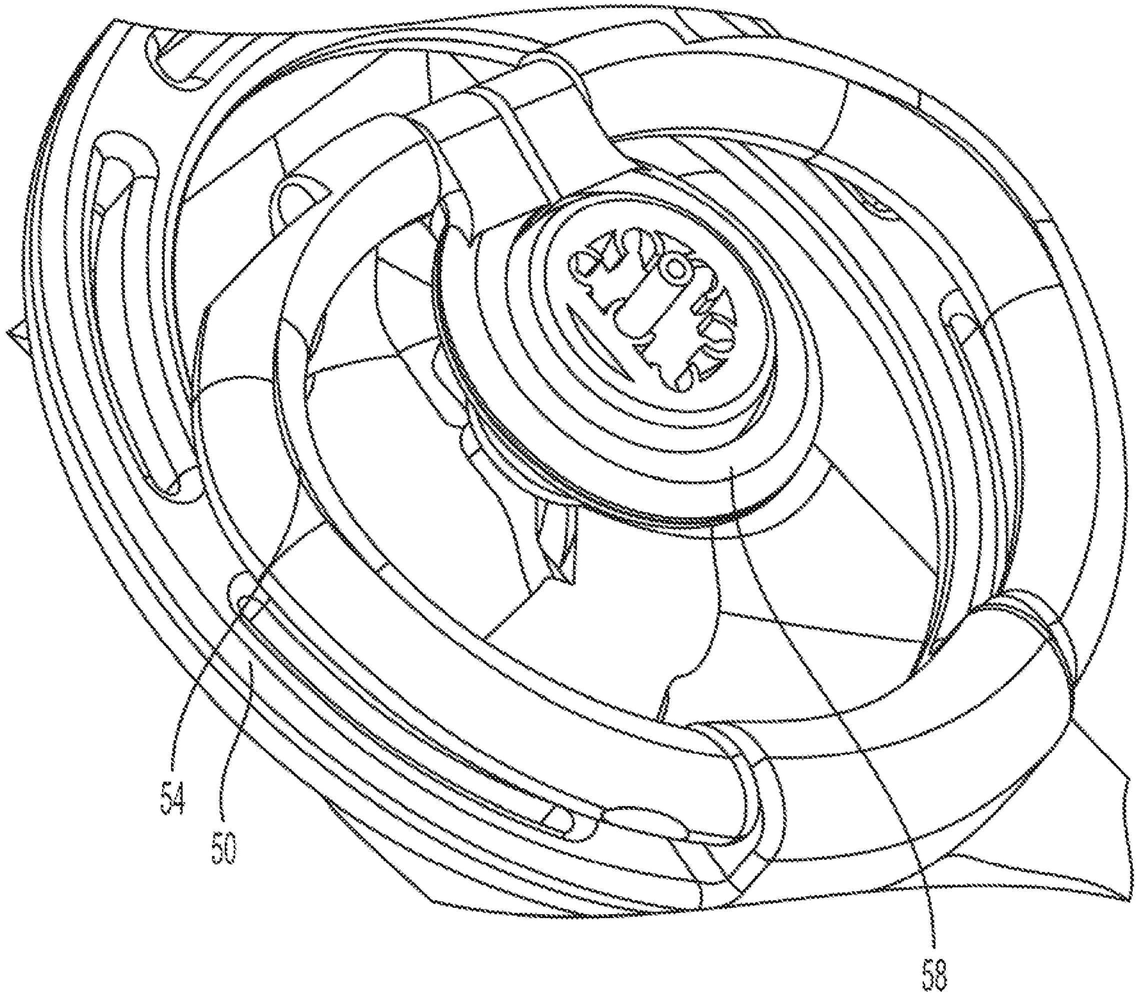
Figure 16D:
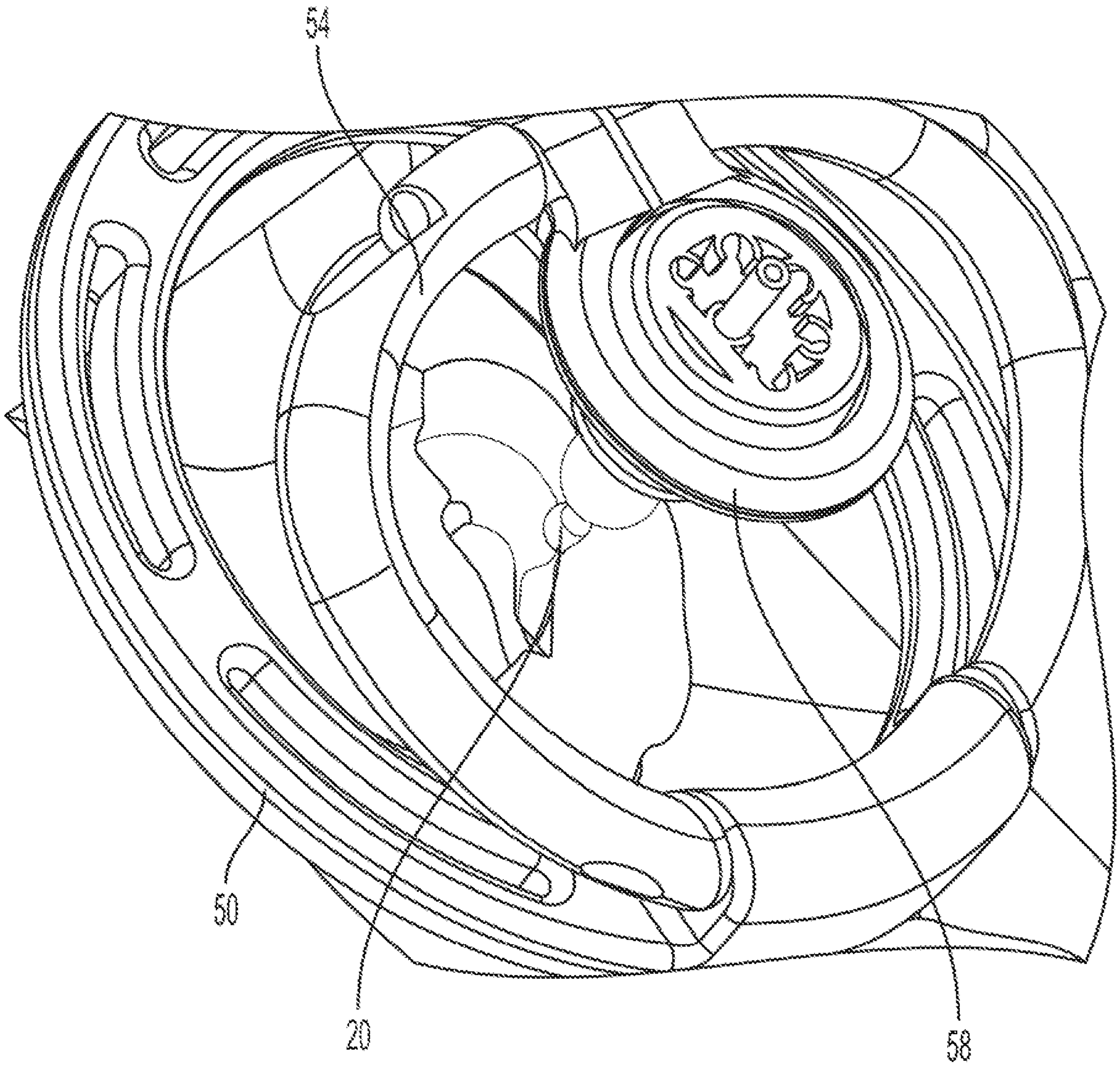

FIG. 16A is a side view of another apparatus for providing stimulation in accordance with embodiments disclosed herein. FIG. 16B is a schematic diagram of a front view of a strap or band supporting a pair of apparatuses for providing stimulation. FIG. 16C is a perspective view of the stimulation apparatus as in 16A in a first configuration in which a third body of the housing is in a first spacing from the ear of the patient. FIG. 16D is a perspective view of the stimulation apparatus as in 16C in a second configuration in which the third body of the housing is in a second spacing from the ear of the patient that is greater than the first spacing. (i.e., the third body is shifted away from the ear relative to the perspective view of FIG. 16C.)

Figure 17:
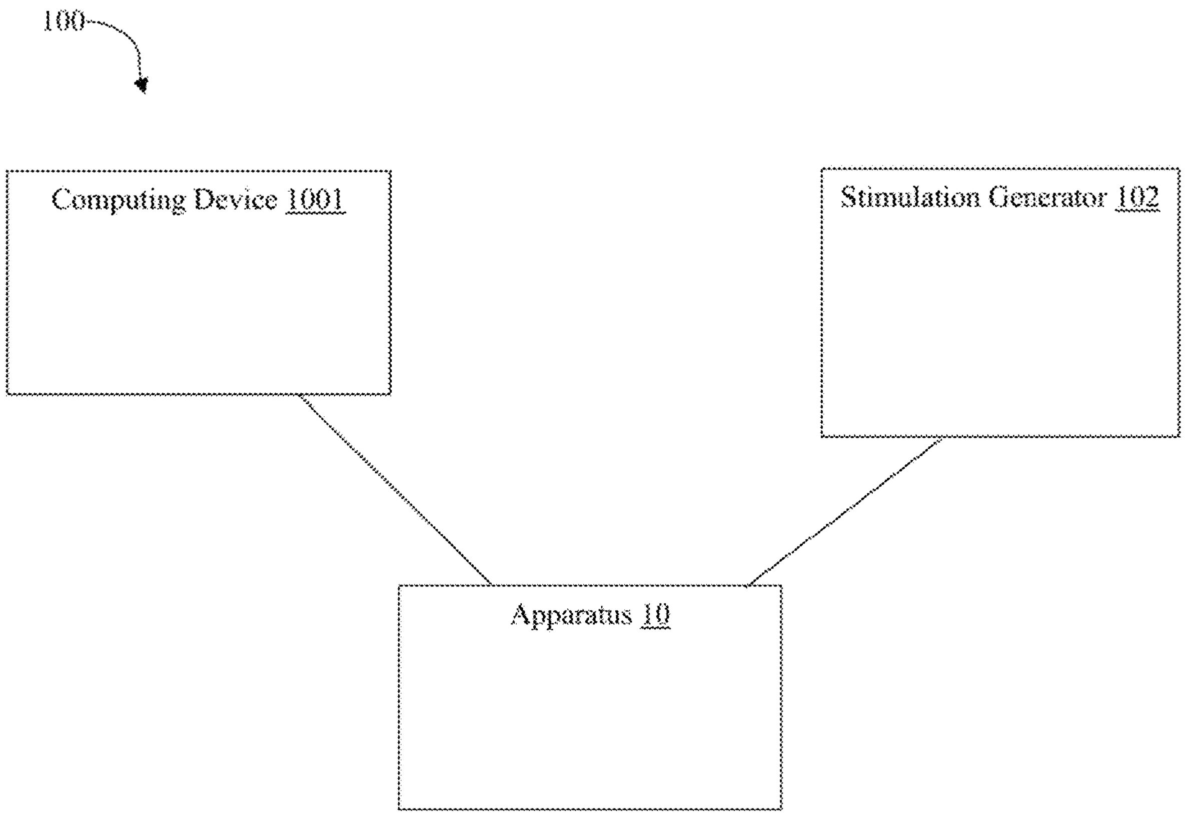

FIG. 17 is a system for providing stimulation as disclosed herein.

Figure 18:
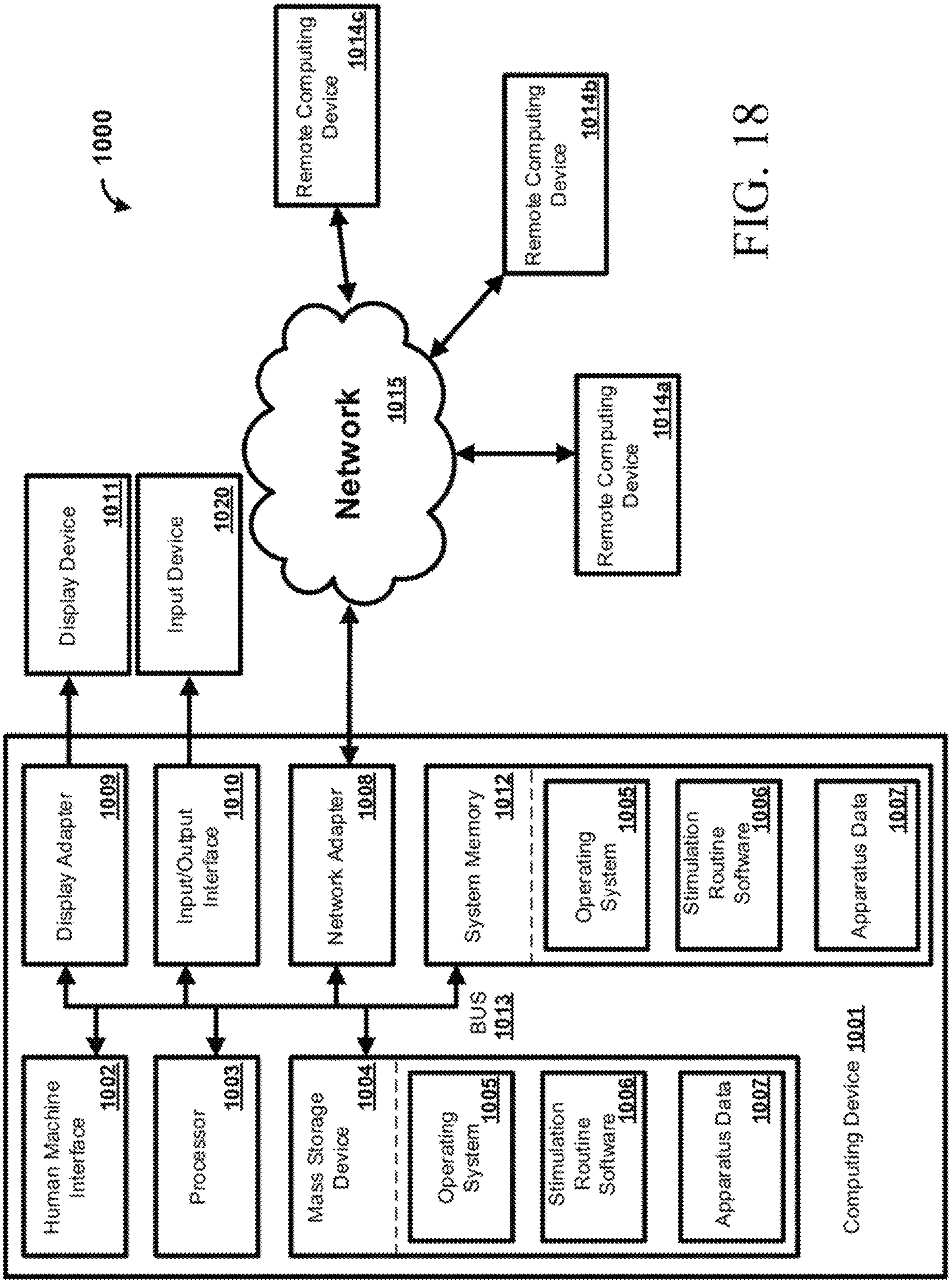

FIG. 18 is an exemplary computing device of the system of FIG. 14.

Figure 19B:
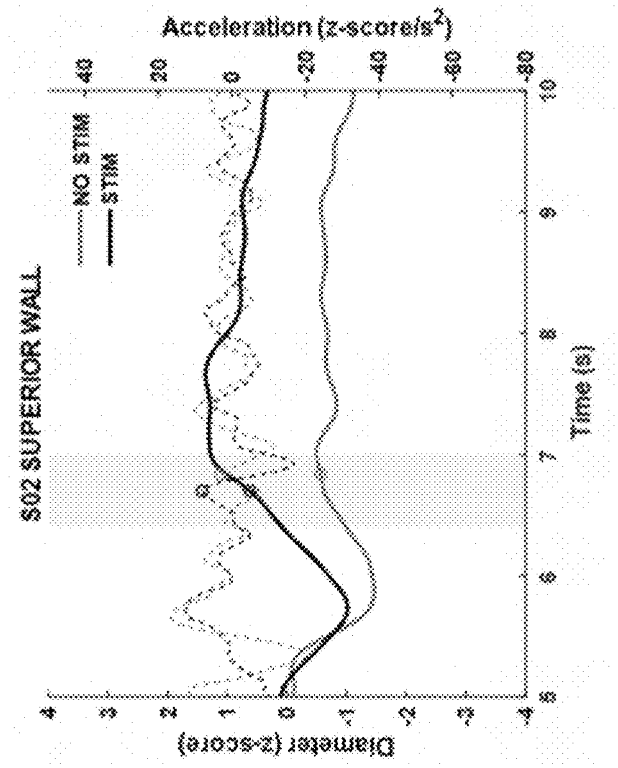
Figure 19A:
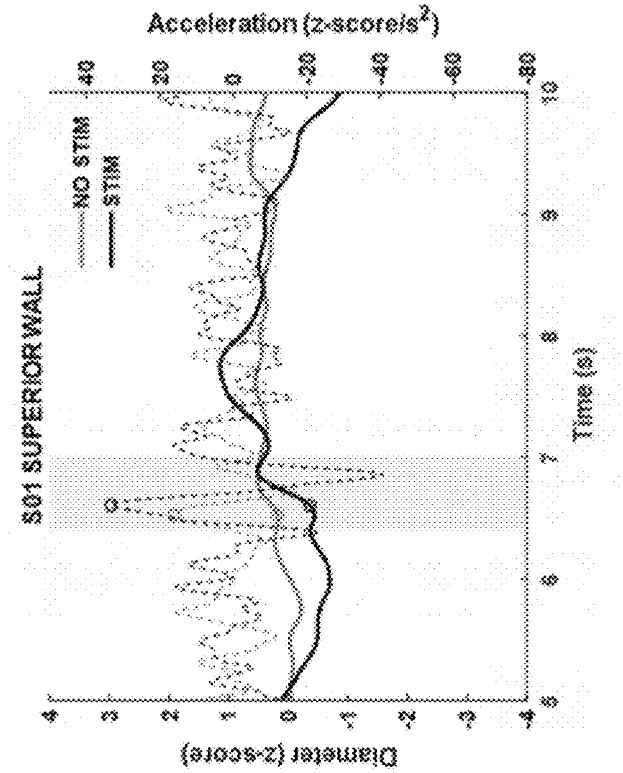
Figure 19C:
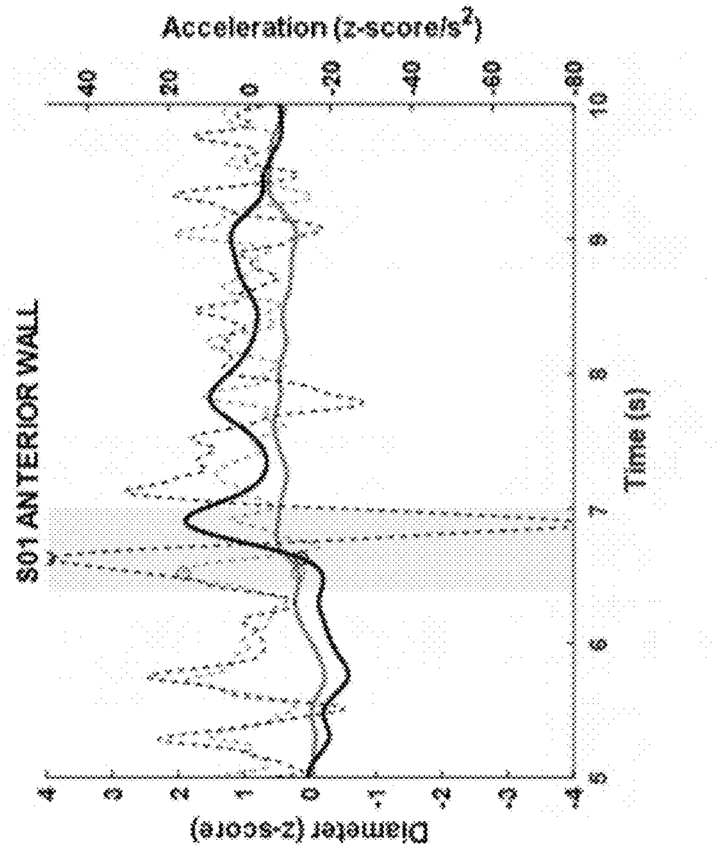
Figure 19D:
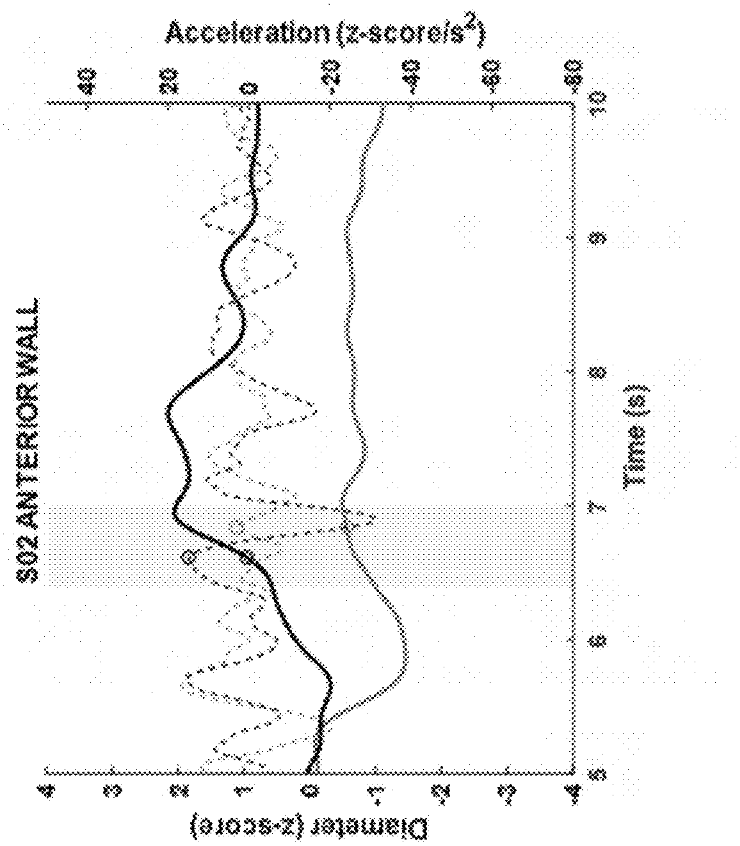
Figure 19F:
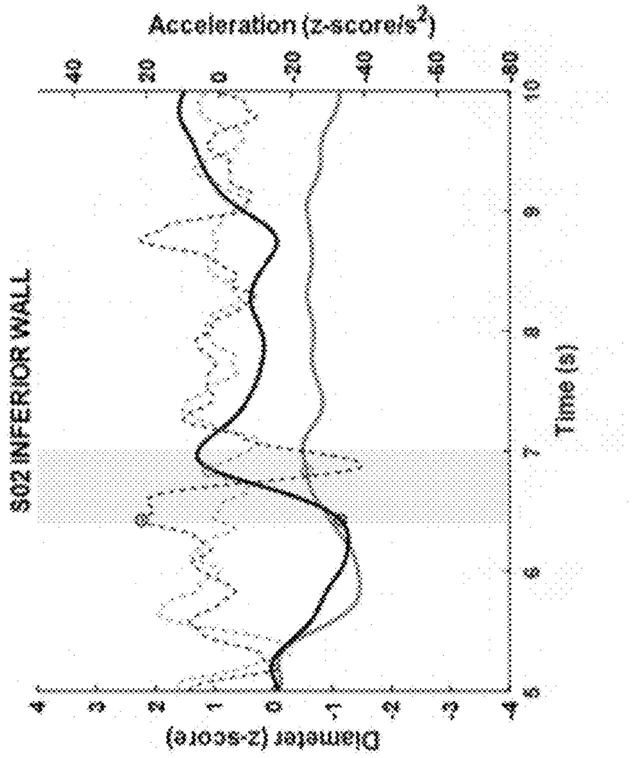
Figure 19E:
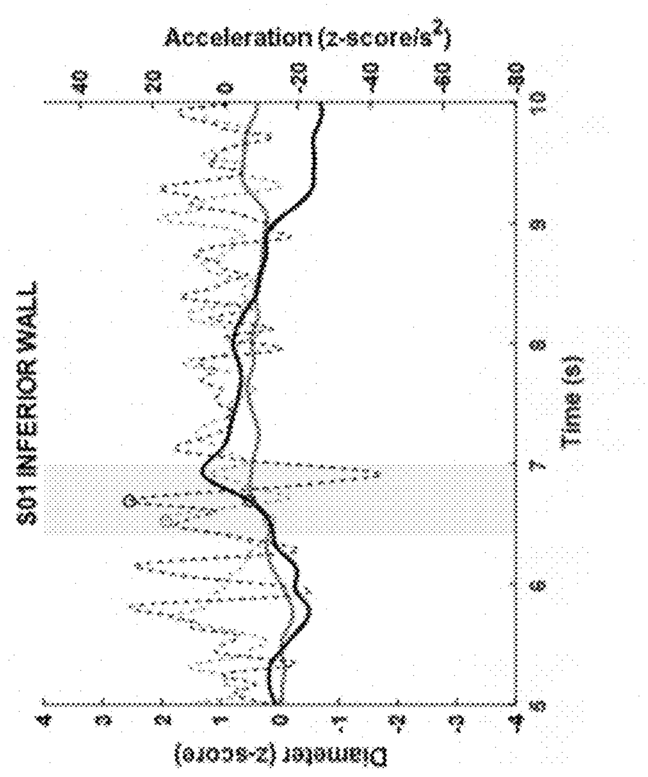
Figure 19H:
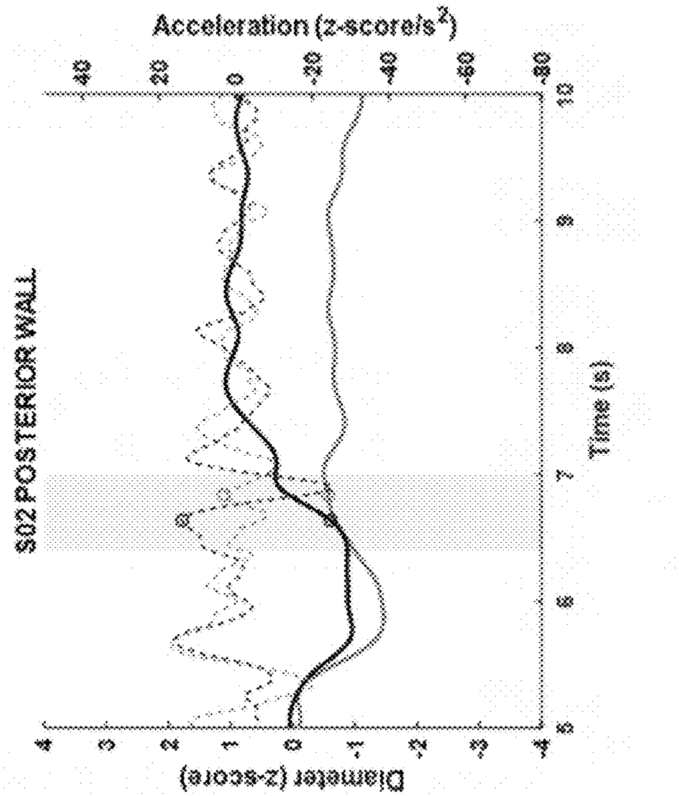
Figure 19G:
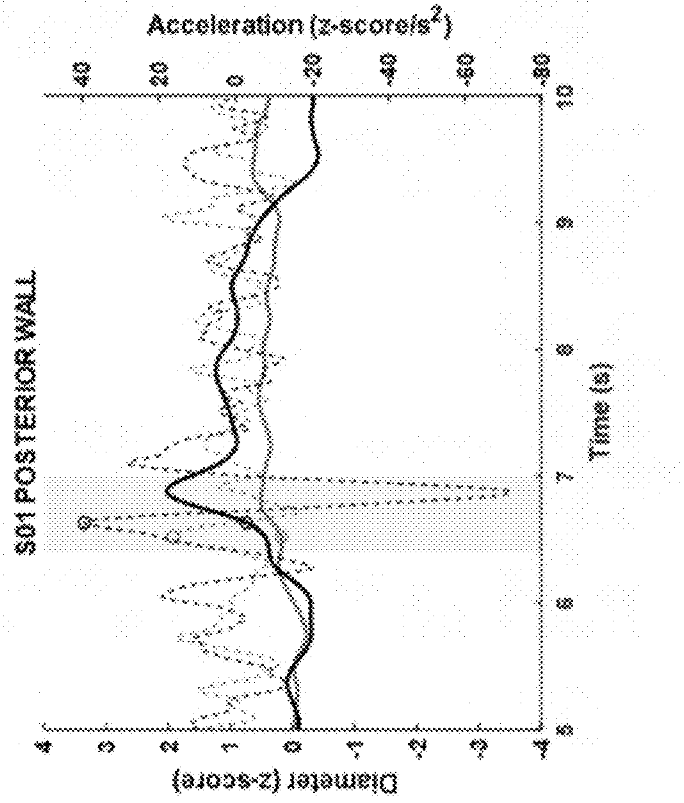

FIG. 19A-B show waveform-averaged pupil diameter recordings when stimulating on the superior wall of each canal wall in two subjects (S01 and S02) at a fixed stimulation amplitude and frequency. FIG. 19C-D show waveform-averaged pupil diameter recordings when stimulating on the anterior wall of each canal wall in the two subjects at a fixed stimulation amplitude and frequency. FIG. 19E-F show waveform-averaged pupil diameter recordings when stimulating on the inferior wall of each canal wall in the two subjects at a fixed stimulation amplitude and frequency. FIG. 19G-H show waveform-averaged pupil diameter recordings when stimulating on the posterior wall of each canal wall in the two subjects at a fixed stimulation amplitude and frequency.

DETAILED DESCRIPTION

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or arc products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and CE are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "an electrical pulse" includes a plurality of such electrical pulses, reference to "the subject*" is a reference to one or more subjects and equivalents thereof known to those skilled in the art, and so forth.

The term "auricular vagus nerve stimulation" refers to the stimulating or activating of afferent fibers of the vagus nerve through the external ear. There are established anatomical contacts between the vagus nerve and locus coeruleus via the nucleus tractus solitarius. The locus coeruleus is principally responsible for the release of norepinephrine in the brain. The target of auricular vagus nerve stimulation is locus coeruleus, effectively activating noradrenergic neuronal mechanisms. Other monoaminergic (e.g., serotonergic, dopaminergic) and neurotransmitter systems (e.g., GABAergic, cholinergic) can be primarily or secondarily activated by noninvasive and invasive vagus nerve stimulation.

As used herein, the term "subject," "patient," or "individual" can be used interchangeably and refer to any organism to which an electrical pulse of this invention may be applied or administered, e.g., for experimental, diagnostic, and/or therapeutic purposes. Typical subjects include animals (e.g., mammals such as non-human primates, and humans; avians; domestic household or farm animals such as cats, dogs, sheep, goats, cattle, horses and pigs; laboratory animals such as mice, rats and guinea pigs; rabbits; fish; reptiles; zoo and wild animals). Typically, "subjects" are animals, including mammals such as humans and primates; and the like. The term does not denote a particular age or sex.

By "treat" is meant to administer or apply a therapeutic, such as an electrical pulse, to a subject, such as a human or other mammal (for example, an animal model), that has a disease or disorder that can be treated by vagus nerve stimulation or has an increased susceptibility for developing a disease or disorder that can be treated vagus nerve stimulation, in order to prevent, reduce, or delay a worsening of the effects or symptoms of the disease or disorder, to partially or fully reverse the effects or symptoms of the disease or disorder, or ameliorate a symptom of the disease or disorder (e.g. psychiatric and neurologic disorders and chronic inflammatory disorders).

By "ameliorate" is meant to a lessen at least one indicator, sign, or symptom of an associated disease, disorder, or condition. The severity of indicators may be determined by subjective or objective measures, which are known to those skilled in the art.

By "prevent" is meant to minimize the chance that a subject who has an increased susceptibility for developing a disease or disorder that can be treated vagus nerve stimulation will develop the disease or disorder or symptoms associated with the disease or disorder.

The phrase "acute activation" or "acutely activating" refers to activation that occurs on millisecond timescales during the time course and/or immediately following the time of stimulation. For example, acutely activating the noradrenergic system refers to activating the noradrenergic system at the time of a vagus nerve stimulation (e.g. auricular vagus nerve stimulation) or less than 1 second thereafter.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinence of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Methods of Acutely Activating the Noradrenergic System

The vagus nerve has been a target of neuromodulation technologies that aim to treat symptoms associated with a wide array of disease states. Noninvasive approaches have been developed to overcome the need for surgical procedures and to avoid the cost of implantable systems. Demonstration of acute autonomic engagement by way of noninvasive approaches is needed to confirm that the targeted neural pathways are activated to elicit the intended effect(s). Evidence to this end is also a necessary step for therapeutic applications that require synchronized activation of relevant neural pathways via vagus nerve recruitment with behavioral, environmental, or task-related events. Data presented here demonstrate that brief pulse trains of electrical current applied to external ear anatomical landmarks drive an acute, autonomic response from the noradrenergic system in humans, enhancing the potential of targeted neuromodulation used to enhance learning across a variety of human performance contexts and to improve quality of life for individuals suffering from chronic health conditions.

The noradrenergic system, when activated, exerts effects in many areas of the nervous system. Noradrenergic neurons (i.e., neurons whose primary neurotransmitter is norepinephrine) are comparatively few in number, and their cell bodies are confined to a few relatively small brain areas, but they send projections to many other brain areas and exert powerful effects on their targets. Vagus nerve stimulation can provide surges in norepinephrine in the brain, thus activating the noradrenergic neurons/system. The vagus nerve can be engaged via recruitment of the auricular branch which allows the vagus nerve to activate brainstem nuclei which is responsible for the release of norepinephrine and other monoamines/neurotransmitters.

Disclosed are methods comprising applying one or more electrical pulses to an ear of a subject, wherein the one or more electrical pulses are sufficient to acutely activate the noradrenergic system of the subject. In some aspects, "electrical pulse" can be used interchangeably with "electrical impulse." In some aspects, one or more electrical pulses is the same as one or more pulses of electrical current. In some aspects, one or more electrical pulses comprise a stimulation train and several stimulation trains can be applied in the context of a single treatment or application. In some aspects, a stimulation train is a group of electrical impulses that are close together in time.

Disclosed are methods of acutely activating the noradrenergic system in a subject comprising applying one or more electrical pulses to an car of the subject, wherein the one or more electrical pulses are sufficient to acutely activate the noradrenergic system of the subject.

In some aspects, acutely activating the noradrenergic system comprises stimulating the vagus nerve. In some aspects, acutely activating the noradrenergic system comprises an activation that can last long after stimulation has ended. In some aspects, acutely activating the noradrenergic system comprises a stimulation that engages the target (i.e., noradrenergic mechanism) on short/millisecond time scales (i.e., less than 1 s).

In some aspects, one or more electrical pulses can be applied to the external ear of a subject. In some aspects, the ear canal of a subject can be applied to one or more electrical pulses. In some aspects, the ear canal can also be referred to as the external acoustic meatus. In some aspects, one or more electrical pulses can be applied to the cymba and cavum concha of a subject. In some aspects, one or more electrical pulses can be applied to the tragus of the subject. In some aspects, stimulating the ear with one or more electrical pulses can also be referred to as transcutaneous auricular vagus nerve stimulation (taVNS). taVNS refers to a noninvasive stimulation that can result in acute activation of the noradrenergic system.

In some aspects, the one or more electrical pulses are applied unilaterally to the subject. In some aspects, the one or more electrical pulses are applied only to the external ear of the subject. In some aspects, one or more electrical pulses can be applied to the cymba and cavum concha of a subject. In some aspects, the one or more electrical pulses are applied only to the left ear of the subject. In some aspects, the one or more electrical pulses are applied only to the external ear of the left ear of the subject. In some aspects, the one or more electrical pulses are applied only to the ear canal of the left ear of the subject. In some aspects, one or more electrical pulses can be applied to the tragus of the left ear of the subject. Thus, in some aspects, one or more electrical pulses are not applied to the right ear of the subject. In some aspects, the one or more electrical pulses are applied only to the right ear of the subject. In some aspects, the one or more electrical pulses are applied only to the external ear of the right ear of the subject. In some aspects, the one or more electrical pulses are applied only to the ear canal of the right ear of the subject. In some aspects, one or more electrical pulses can be applied to the tragus of the right car of the subject. Thus, in some aspects, one or more electrical pulses are not applied to the left ear of the subject.

In some aspects, the one or more electrical pulses are applied bilaterally to the subject. Thus, in some aspects, the one or more electrical pulses are applied to both the right and left ear of the subject.

Acute activation of the noradrenergic system can be important for therapeutic applications. In some aspects, activation of the noradrenergic system must coincide with an environmental, behavioral, or task-related event in order for the activation to provide a therapeutic effect. For example, activation can be via auricular vagus nerve stimulation that is provided or occurs at approximately the same time as an environmental, behavioral, or task-related event and can result in a therapeutic effect. Examples of an environmental, behavioral, or task-related event can be, but are not limited to, exposure to noxious stimulus that is otherwise benign, but through negative association, becomes noxious. Additional examples of behavioral events include performance of a motor or cognitive task.

In some aspects, applying one or more electrical pulses to the ear of the subject comprises positioning an object or device within the ear of the subject and generating electrical pulses with the object or device, wherein the electrical pulses are transmitted through the car to the vagus nerve in the subject. In some aspects, the object or device can be one or more cylindrical or spherical electrodes. In some aspects, positioning a device within the ear of the subject comprises positioning a cylindrical or spherical electrode wrapped in or treated with conductive material within the ear of the subject. In some aspects, the methods can further comprise positioning a return via a snap electrode on a lateral mastoid or spinous process.

The ear comprises an auricular branch of the vagus nerve. In some aspects, the auricular branch of the vagus nerve is in the external ear. The vagus nerve is comprised of afferent fibers, such that the electrical current is transduced into neural signals that are, in turn, transmitted to the central nervous system (CNS). The auricular branch of the vagus nerve contains innervation beneath the skin surface of the external ear in the external auditory meatus, inner tragus, and concha.

In some aspects, activation of the noradrenergic system is confirmed by presence of pupil dilation. In some aspects, assessing pupil dilation comprises looking for a change in pupil diameter. In some aspects, activation of the noradrenergic system can be confirmed by the change in pupil diameter, wherein the change in pupil diameter is an increase in pupil dilation. In some aspects, assessing pupil dilation comprises establishing perceptual thresholds of auricular stimulation and measuring changes in pupil dilation from baseline to after stimulation onset. In some aspects, establishing perceptual thresholds comprises determining the minimum electrical current needed to evoke a percept (ie. conscious awareness that a stimulus is present) from a subject. In some aspects, measuring changes in pupil dilation while stimulating specific landmarks or locations on the external ear can be performed at electrical current amplitudes of 0 mA, below the established perceptual threshold, at the established perceptual threshold, and/or above the established perceptual threshold.

In some aspects, the one or more electrical pulses are administered at a frequency of between 1 Hz and 10,000 Hz. In some aspects, the one or more electrical pulses are administered at a frequency of between 100 Hz and 300 Hz, between 200 Hz and 400 Hz, between 250 Hz and 350 Hz, between 300 Hz and 400 Hz. In some aspects, the one or more electrical pulses are administered at a frequency of 100, 150, 200, 250, 300, 350, 400, 450, or 500 Hz. In some aspects, the one or more electrical pulses are administered at a frequency of 100, 1000, 2000, 3000, 4000, 5000, 6000, 7000, 8000, 9000, or 10,000 Hz. In some aspects, the one or more electrical pulses are administered at a frequency of 300 Hz.

In some aspects, applying one or more electrical pulses to an ear of the subject occurs for a duration of about 1 ms to 1000 ms. In some aspects, applying one or more electrical pulses to an car of the subject occurs for a duration of about 500 ms to 800 ms. In some aspects, applying one or more electrical pulses to an ear of the subject occurs for a duration of about 100, 150, 200, 250, 300,350, 400, 450, 500, 550, 600, 650, 700, 750, or 800 ms. In some aspects, applying one or more electrical pulses to an ear of the subject occurs for a duration of about 30 seconds to 30 minutes. In some aspects, applying one or more electrical pulses to an ear of the subject occurs for a duration of about 1, 2, 3, 4, 5, 6, 7, 8, 9, 10, 15, 20, 25, or 30 minutes.

In some aspects, applying one or more electrical pulses to an ear of the subject occurs with a pulse width of 100 μs and 1,000 μs. In some aspects, the one or more electrical pulses have a pulse width of between 100 μs and 300 μs, between 200 μs and 400 μs, between 250 μs and 350 μs, between 300 μs and 400 μs. In some aspects, the one or more electrical pulses have a pulse width of 100, 150, 200, 250, 300, 350, 400, 450, or 500 μs. In some aspects, the one or more electrical pulses have a pulse width of 300 μs.

In some aspects, the current amplitude can be normalized on a subject by subject basis. Because the current amplitude is determined based on perceptual threshold and each subject can have a slightly varied perceptual threshold, the current amplitude is not necessarily a set value. Although the current amplitude can vary from subject to subject, in some aspects there can be a critical window since changes in arousal levels resulting from the release of neurotransmitter, which is released upon auricular vagus nerve stimulation, can interfere with learning and/or performance. Thus, the current amplitude can be titrated relative to perceptual threshold in a way that promotes learning. In some aspects, the amplitude can be 0-10 mA.

C. Methods of Supporting Learning or Treating Symptoms of Clinical Disorders

Disclosed herein are methods of supporting learning or re-learning in a subject. Disclosed herein are methods in a subject comprising applying one or more electrical pulses to an ear of the subject, wherein the one or more electrical pulses are sufficient to acutely activate the noradrenergic system of the subject thereby supporting learning in the subject. For example, stimulating the vagus nerve to activate the noradrenergic system allows enhanced memory consolidation during motor learning or re-learning. For example, a subject having undergone a stroke can undergo motor rehabilitation to re-train muscles weakened by or movements impaired by the stroke. Vagus nerve stimulation, such as taVNS, can enhance the effect of the re-training. In some aspects, vagus nerve stimulation must be paired with re-trained movements and not delayed to allow activation of the noradrenergic system to coincide with movements.

Disclosed are methods of treating a subject in need thereof comprising applying one or more electrical pulses to an ear of the subject, wherein the one or more electrical pulses are sufficient to acutely activate the noradrenergic system of the subject in need thereof. In some aspects, a subject in need thereof can be a subject who has suffered a stroke. In some aspects, a subject in need thereof can be a subject having a psychiatric disorder, neurological disorder, chronic inflammatory disorder, or other disorder. In some aspects, the psychiatric disorder can be, but is not limited to, post-traumatic stress disorder (PTSD), anxiety, depression, or substance abuse. In some aspects, the neurologic disorders can be, but are not limited to, paretic syndrome (i.e., muscle weakness, spasticity, etc.) resulting from damage to the corticospinal tract due to stroke, spinal cord injury, or traumatic brain injury. In some aspects, other neurological disorders can be, but are not limited to epilepsy, nystagmus, neuropathic pain, disorders of cognition/consciousness, or tinnitus. In some aspects, the chronic inflammatory disorders can be fibromyalgia, migraine headaches, or obesity. In some aspects, other disorders can be lung injury, cardiovascular disease/atherosclerosis, or diabetes. In some aspects, a subject in need thereof is a healthy subject. For example, any healthy subject can be treated with one or more electrical pulses in the ear to acutely activate the noradrenergic system of the subject in order to facilitate learning in the subject.

Disclosed are methods of treating a disease or disorder in a subject comprising applying one or more electrical pulses to an ear of the subject, wherein the one or more electrical pulses are sufficient to acutely activate the noradrenergic system of the subject such that the disease or disorder in the subject is treated. In some aspects, the disease or disorder can be a psychiatric disorder, neurological disorder, chronic inflammatory disorder, or other disorders. In some aspects, the psychiatric disorder can be, but is not limited to, post-traumatic stress disorder (PTSD), anxiety, depression, or substance abuse. In some aspects, the neurologic disorders can be, but are not limited to, paretic syndrome (i.e., muscle weakness, spasticity, etc.) resulting from damage to the corticospinal tract due to stroke, spinal cord injury, or traumatic brain injury. In some aspects, other neurological disorders can be but are not limited to epilepsy, nystagmus, neuropathic pain, disorders of cognition/consciousness, or tinnitus. In some aspects, the chronic inflammatory disorders can be fibromyalgia, migraine headaches, or obesity. In some aspects, other disorders can be lung injury, cardiovascular disease/atherosclerosis, or diabetes.

Disclosed are methods of treating a disease or disorder in a subject comprising applying one or more electrical pulses to an ear of the subject, wherein the one or more electrical pulses are sufficient to acutely activate the noradrenergic system of the subject, wherein acute activation of the noradrenergic system extinguishes conditioned fears through repeated reminders of traumatic events. In some aspects, exposure therapy can extinguish conditioned fears through repeated reminders of traumatic events. Extinction of the conditioned fear can depend on the consolidation of new memories made with these exposures. In some aspects, traumatic events lead to activation of the sympathetic nervous system via the flight-or-fight response. The resulting peripheral changes, such as increased heart and respiration rate, can occur during the memory consolidation window and can be associated with enhanced memory storage. In some aspects, however, epinephrine does not readily cross the blood-brain barrier. Rather, epinephrine can bind to beta-adrenergic receptors on the vagus nerve, which then activate brainstem nuclei to release norepinephrine throughout the brain, leading to storage of a newly acquired memory. In some aspects, vagus nerve stimulation can serve as an adjunct therapy to improve consolidation maintenance of the extinction memory, as it promotes neural plasticity but bypasses the peripheral fight-or-flight response. Rather, vagus nerve stimulation can engage parasympathetic pathways, slowing heart rate and increasing gut motility. Pairing vagus nerve stimulation with exposure therapy, therefore, can strengthen the extinction memory by tapping into mechanisms that enhance storage of the memory without eliciting the sympathetic stress response.

Disclosed are methods of treating a disease or disorder in a subject comprising applying one or more electrical pulses to an ear of the subject, wherein the one or more electrical pulses are sufficient to acutely activate the noradrenergic system of the subject, wherein acute activation of the noradrenergic system improves consolidation and maintenance of the extinction memory.

Disclosed are methods of ameliorating a symptom associated with a psychiatric disorder, neurological disorder, or chronic inflammatory disorder in a subject comprising applying one or more electrical pulses to an ear of the subject, wherein the one or more electrical pulses are sufficient to ameliorate a symptom associated with a psychiatric disorder, neurological disorder, chronic inflammatory, or other disorder in a subject. In some aspects, the psychiatric disorder, neurological disorder, chronic inflammatory, or other disorder are any of those disclosed herein. In some aspects, a symptom associated with a psychiatric disorder, neurological disorder, chronic inflammatory, or other disorder can be, but is not limited to, seizures, generalized perceptions of pain, feelings of sadness and/or hopelessness, irritability, loss of interest, decrease sleep disturbance, increase appetite, enhanced cognition, decrease feelings of worthlessness, thoughts of self-harm/suicide, intrusive thoughts/flashbacks, irritability and hypervigilance, altered motor function. Thus, any one or more of the disclosed symptoms can be ameliorated Disclosed are methods to support learning in a subject in need thereof comprising applying one or more electrical pulses to an ear of the subject, wherein the one or more electrical pulses are sufficient to acutely activate the noradrenergic system of the subject in need thereof, wherein the subject in need thereof has enhanced learning. In some aspects, a subject in need thereof can be a healthy individual. In some aspects, a subject in need thereof can be a subject that has suffered a stroke. In some aspects, a subject in need thereof can be a subject having a psychiatric disorder, neurologic disorder, chronic inflammatory disorder, or other disorder. In some aspects, the psychiatric disorder, neurological disorder, chronic inflammatory, or other disorder are any of those disclosed herein.

In some aspects, "electrical pulse" can be used interchangeably with "electrical impulse." In some aspects, one or more electrical pulses is the same as one or more pulses of electrical current. In some aspects, one or more electrical pulses comprise a stimulation train and several stimulation trains can be applied in the context of a single treatment or application. In some aspects, a stimulation train is a group of electrical impulses that are close together in time.

In some aspects in any of the disclosed methods, the one or more electrical pulses are applied unilaterally to the subject. In some aspects, the one or more electrical pulses are applied only to the external ear of the subject. In some aspects, one or more electrical pulses can be applied to the cymba and cavum concha of a subject. In some aspects, one or more pulses can be applied to the tragus of a subject. In some aspects, the one or more electrical pulses are applied only to the left ear of the subject. In some aspects, the one or more electrical pulses are applied only to the external ear of the left ear of the subject. In some aspects, the one or more electrical pulses are applied only to the ear canal of the left ear of the subject. Thus, in some aspects, one or more electrical pulses are not applied to the right ear of the subject. In some aspects, the one or more electrical pulses are applied only to the right ear of the subject. In some aspects, the one or more electrical pulses are applied only to the external ear of the subject. In some aspects, the one or more electrical pulses are applied only to the car canal of the right ear of the subject. Thus, in some aspects, one or more electrical pulses are not applied to the left ear of the subject.

In some aspects in any of the disclosed methods, the one or more electrical pulses are applied bilaterally to the subject. Thus, in some aspects, the one or more electrical pulses are applied to both the right and left ear of the subject.

In some aspects, applying one or more electrical pulses to the vagus nerve of the subject comprises applying according to a treatment paradigm. A treatment paradigm is a schedule or program of treatments designed for treating a disease or disorder or treating a symptom of a disease or disorder. In some aspects, the treatment paradigm comprises a one or more electrical pulses for a time period of about 1 ms to 1000 ms. In some aspects, the treatment paradigm comprises one or more electrical pulses for a time period of about 500 ms to 800 ms. In some aspects, the treatment paradigm comprises one or more electrical pulses for a time period of about 100, 150, 200, 250, 300, 350, 400, 450, 500, 550, 600, 650, 700, 750, or 800 ms. In some aspects, the treatment paradigm comprises continuously applying the electrical pulses for a time period of about 1 ms to 1000 ms. In some aspects, the treatment paradigm comprises one or more electrical pulses for a time period of about 30 seconds to 30 minutes. In some aspects, the treatment paradigm comprises one or more electrical pulses for a time period of about 1, 2, 3, 4, 5, 6, 7, 8, 9, 10, 15, 20, 25, or 30 minutes. In some aspects, a treatment paradigm comprises one or more electrical pulses comprising a stimulation train or several stimulation trains in a single treatment. In some aspects, the one or more electrical pulses coincides with an environmental event or a behavior therefore helping in learning the environmental event or behavior.

In some aspects, applying one or more electrical pulses occurs with a pulse width of 100 μs and 1,000 μs. In some aspects, the one or more electrical pulses have a pulse width of between 100 μs and 300 μs, between 200 μs and 400 μs, between 250 μs and 350 μs, or between 300 μs and 400 μs. In some aspects, the one or more electrical pulses have a pulse width of 100, 150, 200, 250, 300, 350, 400, 450, or 500 μs. In some aspects, the one or more electrical pulses have a pulse width of 300 μs.

In some aspects, the one or more electrical pulses have a frequency of between 1 Hz and 10,000 Hz. In some aspects, the one or more electrical pulses have a frequency of between 100 Hz and 300 Hz, between 200 Hz and 400 Hz, between 250 Hz and 350 Hz, between 300 Hz and 400 Hz. In some aspects, the one or more electrical pulses have a frequency of 100, 150, 200, 250, 300, 350, 400, 450, or 500 Hz. In some aspects, the one or more electrical pulses have a frequency of 300 Hz.

In some aspects, the current amplitude can be normalized on a subject by subject basis. Because the current amplitude is determined based on perceptual threshold and each subject can have a slightly varied perceptual threshold, the current amplitude is not necessarily a set value. Although the current amplitude can vary subject to subject, in some aspects there can be a critical window since too much neurotransmitter, which is released upon auricular stimulation, can interfere with performance. Thus, the current amplitude can be titrated relative to perceptual threshold in a way that promotes learning.

In some aspects, the treatment paradigm is applied once daily. In some aspects, the treatment paradigm is applied at least twice daily. In some aspects, each treatment paradigm is applied within 5 minutes of each other. In some aspects, the treatment paradigm is applied once a week. In some aspects, the treatment paradigm is applied once a month.

In some aspects, acutely activating the noradrenergic system comprises stimulating the vagus nerve of the subject. In some aspects, stimulating the vagus nerve comprises taVNS.

In some aspects of the disclosed methods, the one or more electrical pulses to an ear of the subject are applied simultaneously with a behavior, environmental, or task-related event to be learned. Thus, in some aspects, the one or more electrical pulses to an ear of the subject enhance the learning of the behavior, environmental, or task-related event administered or provided simultaneously.

In some aspects, the disclosed methods to support learning can be used to support learning of any type of skill or activity. In some aspects, the disclosed methods to support learning can be used to support learning how to move one or more body parts; learning how to associate two or more items; learning daily activities such as cooking, cleaning, and self-grooming; learning fundamental motor skills such as walking, miming, jumping; learning sports skills such skiing, kayaking, boarding, golfing; learning language skills such as producing speech, understanding speech, reading, writing, singing; and learning other daily skills such as driving a vehicle, meditating, mathematical computation. In some aspects, the disclosed methods to support learning can be used to support learning any behavior whether it is a learned behavior or innate behavior. For example, an innate behavior can be refined as a process of neural maturation and therefore can be learned in the disclosed methods. In some aspects, environmental events refer to the subjective association one has to perceptual phenomena and can vary based on personal experience.

D. Exemplary Stimulation Apparatus

Referring to FIGS. 10-12 and 14, an apparatus 10 can be configured to provide stimulation as disclosed herein. As should be understood, the treatments described herein should not be limited to use with the particular embodiments of the apparatus 10 described and depicted herein. Rather, the apparatus 10 merely provides an exemplary embodiment for provision of such treatments.

The apparatus 10 can comprise an elongate body 12 having a longitudinal axis 14 and a first end 16 and a second end 18 that are spaced along the longitudinal axis. A first electrode 20 can be positioned at or proximate the first end 16 of the elongate body 12. The first electrode 20 can be configured to be received at least partially in an car canal of an ear. A second electrode 22 can be positioned between the first electrode 20 and the second end 18 of the elongate body 12. The second electrode can serve as a ground electrode. A first conductor 24 can be in electrical communication with the first electrode 20, and a second conductor 26 can be in electrical communication with the second electrode 22. In exemplary aspects, the first and second conductors 24, 26 can comprise electrical wires or cables that are soldered, respectively, to the first and second electrodes 20, 22. Optionally, in these aspects, the first and second conductors 24, 26 can be coupled to or associated with touch-proof connectors as are known the art. However, it is contemplated that the first and second conductors 24, 26 can comprise any electrical wire or cable that is capable of providing electrical stimulation as disclosed herein.

A housing 30 can receive a portion of the elongate body 12 therein. The housing 30 can have a central axis 32. The elongate body 12 can be pivotable relative to the housing 30 about the central axis 32. The housing 30 can be configured to retain the elongate body 12 in a plurality of positions that are onset from each other by at least an azimuthal angle offset. Optionally, the azimuthal angle offset between adjacent positions of the plurality of positions can be between about 10 to about 90 degrees, from about 15 degrees to about 75 degrees, from 30 degrees to about 60 degrees, or about 45 degrees. In various aspects, the azimuthal angle offset between any two adjacent positions can be the same as, or different from, any two other adjacent positions. In some optional aspects, the housing 30 can define a socket 36, which can optionally be spherical. The apparatus 10 can comprise a ball 38 that is pivotably received within the socket 36. Optionally, the ball 38 can have a spherical outer surface. The ball 38 can be fixedly coupled to the elongate body 12 so that the ball and the socket 36 cooperate to enable movement of the elongate body relative to the housing to adjust the azimuthal angle, θ, and a polar angle, φ, of the elongate body relative to the central axis 32 of the housing. As can be understood, the polar angle φ can be the angle between the longitudinal axis 14 of the elongate body 12 and the central axis 32 of the housing 30 (e.g., the angular offset of the longitudinal axis 14 of the elongate body from the central axis 32 of the housing), as shown in FIG. 10. As shown in FIG. 15, the azimuthal angle θ can be the angle corresponding to the pivotal movement of the elongate body 12 about the central axis 32 from any two positions (e.g., between a first position 40*a* and a second position 40*b*). It is contemplated that, in some optional aspects, the elongate body 12 can be pivoted about a 360 degree azimuthal angle θ about the central axis. In some optional aspects, the polar angle φ can be adjusted from 0 degrees (with the longitudinal axis 14 of the elongate body 12 parallel to the central axis 32 of the housing 30) to 45 degrees, or from zero degrees to less than 45 degrees, or from 0 degrees to less than 30 degrees, or from zero degrees to less than 15 degrees.

The housing 30 can further comprise a support element 34 that is configured to support the apparatus at—or removably couple the apparatus to—the ear. In some aspects, the support element 34 can support the apparatus 10 so that the first electrode 20 is at least partially positioned within the ear canal. For example, the support element 34 can comprise a deformable element (optionally, an elongate deformable element) that is configured to at least partially wrap around and/or rest upon an outer ear portion of the ear of the user (e.g., in the manner of an "car hook" as is known in the art). In exemplary aspects, the support element 34 can comprise a wire or cable that retains its shape when bent so that the wire or cable can be configured for a particular user. Optionally, the support element 34 can comprise non-conduct material, such as malleable rubber. The support element 34 can be configured to support the apparatus 10 on the outer ear port of the ear to permit electrical stimulation of a nerve adjacent to the ear canal (e.g., an auricular branch of the vagus nerve). However, when positioned on the ear, it is contemplated that the apparatus 10 can permit stimulation of other portions of the ear canal, such as, for example, upon adjustment of the orientation of the elongate body. In use, it is contemplated that the disclosed apparatus can non-invasively provide electrical stimulation (e.g., an electrical pulse) to an epidermis of the ear, and the electrical stimulation (pulse) can travel through the epidermis and then reach a targeted nerve. Unlike invasive stimulation approaches that require direct contact with a nerve or permanent placement in the vicinity of a nerve, the disclosed non-invasive stimulation approaches do not require direct contact with the nerve and can be easily removed from the ear after stimulation is completed, without the need for any surgical procedure (or recovery from such a surgical procedure).

In some optional aspects, the first electrode 20 can circumferentially surround and extend radially outward from a portion of the elongate body 12. In some optional aspects, the second electrode 22 can circumferentially surround and extend radially outward from a portion of the elongate body 12. In optional exemplary aspects, the first electrode 20 and/or the second electrode 22 can be spherical, or at least partially spherical, or generally spherical or hemispherical (or have a different rounded profile). Optionally, the first electrode 20 can have a first diameter, and the second electrode can have a second diameter that is greater that the first electrode. In further aspects, the first electrode 20 and/or the second electrode 22 can be non-spherical. For example, the first electrode 20 and/or the second electrode 22 can be e.g., cylindrical. In yet further aspects, the first electrode 20 and/or the second electrode 22 can comprise a shape that defines a surface that is complementary to the portion of the ear that it contacts to optimize a contact area with the skin or tissue of the ear. Thus, in some aspects, the first and second electrodes 20,22 need not have the same shape. More particularly, it is contemplated that the first electrode 20 can be configured for complementary receipt within a portion of the ear canal, while the second electrode 22 makes contact with an outer edge of the ear canal (and can be positioned within the tragus). In use, it is contemplated that the first electrode 20 can function as the "active" electrode while the second electrode 22 functions as the "return" electrode.

Optionally, the housing 30 can comprise a retention structure 39 for securing the elongate body at a plurality of positions as disclosed herein. It is contemplated that the retention structure 39 can comprise any fastener or engagement surface that is capable of retaining the elongate body in a desired orientation during use of the apparatus 10 as disclosed herein. Suitable fasteners for retaining the elongate body include, for example, snaps, projections, loops, hoops, and corresponding complementary receptacles or engagement structures that can be positioned at selected positions within or about the housing.

Optionally, in exemplary aspects, the retention structure can comprise a plurality of detents 40. More particularly, the housing can define a respective detent 40 at each of the plurality of positions that are offset from each other by at least an azimuthal angle offset (as further disclosed herein) for retaining the elongate body in the respective detent. As used herein, a detent can be any device or structure for positioning and holding the elongate body 12 in relation to the housing 30 in a manner such that the elongate body 12 can be released by force applied thereto. Optionally, each detent 40 can comprise a socket formed from a resilient material that is configured to flex to receive the elongate body. The socket can define an opening that is smaller than an outer dimension (e.g., diameter) of the elongate body 12 so that, the opening deforms to receive the elongate body and then closes around the elongate body 12 to retain the elongate body in the socket. Optionally, the plurality of detents 40 can be arranged in a circular pattern (FIG. 11). In some optional aspects, the plurality of detents can comprise between 2 and 16 detents (e.g., optionally 2, 3, 4, 6, 8, 10, or 12 detents). The detents can optionally be equally spaced (e.g., circumferentially spaced every 30 or 45 degrees). Alternatively, it is contemplated that the angular spacing between sequential detents can be variable, with some detents spaced apart by an angle that is greater than or less than at least one other pair of sequential detents. In further aspects, and with reference to FIG. 15, the plurality of detents 40 can be arranged in a non-circular pattern. For example, the plurality of detents can be arranged in a D-shape pattern. The flat side of the D-shape can be positioned forwardly toward the face of the user.

In further optional aspects, the retention structure 39 can comprise any anchor or immobilizing structure that holds the elongate body 12 in a desired position relative to the housing 30. For example, the retention structure 39 can comprise one or more locking pins or locking screws that serve to immobilize the elongate body 12 relative to the housing 30.

In some aspects, the second end 18 of the elongate body 12 can extend from the housing 30 by a sufficient distance to serve as a toggle to allow a clinician to grip and orient the elongate body in one of the plurality of positions. For example, the second end 18 of the elongate body 12 can extend from the housing 30 by at least 1 cm, at least 2 cm, or between 1 cm and 8 cm, or between 2 cm and 4 cm, or about 2 cm.

Optionally, the first conductor 24 can extend through at least a portion of (optionally, an entirety of) the elongate body 12, which can define a hollow interior with sufficient space to accommodate the first conductor (and, optionally, the second conductor). In further aspects, at the second conductor 26 can extend through at least a portion of the elongate body 12 (e.g., from the second electrode to the second end 18 of the elongate body). In further aspects, the first and/or second conductor does not extend through the elongate body 12. In some exemplary aspects, the first conductor 24 can extend through the elongate body 12, while the second conductor 26 does not extend through the elongate body. In various aspects, the first and second conductors 24, 26 can couple to interior portions of the respective first and second electrodes 20, 22. In some aspects, and as shown in FIG. 10, the second conductor 26 can couple (e.g., via solder coupling) to an outer surface of the second electrode 22 (on a side of the second electrode opposite the side that engages the ear) and then extend through the elongate body 12.

In various aspects, the first electrode 20 can be spaced from the second electrode 22 along the longitudinal axis 14 of the elongate body. For example, the first electrode 20 can be spaced from the second electrode by between about 1 mm and about 25 mm, or at least 3 mm, or at least 10 mm, or at least 20 mm, or between 3 mm and 20 mm or between 3 mm and 10 mm. The first and second electrodes 20, 22 can each comprise any suitable conductive material. In some optional aspects, the conductive material can be, for example, silver or copper.

Referring to FIG. 13, in some aspects, the housing 30 can comprise a main body 42 and a faceplate 44 that cooperate to retain the ball 38 within the socket 36. The elongate body 12, the ball 38, the first electrode 20 and the second electrode 22 can form a probe 48. The main body 42 and the faceplate 44 can be releasably coupled via fasteners 46. In this way, the probe 48 can be removed for cleaning or replacement. Optionally, a kit can comprise a housing 30 and a plurality of subassemblies 48, wherein the subassemblies differ in at least one of a spacing between the first electrode and the second electrode, a dimension of the first electrode, a dimension of the second electrode, a shape of the first electrode, or a shape of the second electrode. Thus, the probe 48 can be selected for a particular ear canal depth or diameter, etc. Accordingly, the probe 48 can be selected and assembled with the housing 30 to fit a particular user.

In some optional aspects, a method of using the apparatus 10 can comprise positioning the support element 34 relative to the outer ear portion of the ear to support the apparatus on the outer ear portion of the ear with the first electrode positioned in the ear canal. The elongate body can be moved to a first position of the plurality of positions. In this way, the first electrode 20 can be positioned for stimulating at a particular location (e.g., proximate to a particular auricular branch of the vagus nerve or other landmark within the ear canal). With the first electrode so positioned (with the elongate body in the first position), electrical stimulation can be provided between or through the first and second electrodes.

The elongate body can be moved to a second position of the plurality of positions to reposition the first electrode 20. Electrical stimulation can then be provided between or through the first and second electrodes with the elongate body 12 at the second position.

In some aspects, the ear canal comprises an inferior wall, a superior wall, an anterior wall, and a posterior wall. When the elongate body is in the first position, the first electrode is in contact with one of the inferior wall, the superior wall, the anterior wall, or the posterior wall, wherein, when the elongate body is in the second position, the first electrode is in contact with another of the inferior wall, the superior wall, the anterior wall, or the posterior wall. In this way, different auricular branches of the vagus nerve can be stimulated.

The apparatus 10 can be removed the ear of a first test subject and positioned on an ear of a second test subject. For example, the support element can be positioned relative to an outer ear portion of an ear of the second test subject to support the apparatus on the outer ear portion of the ear of the second test subject with the first electrode positioned in an ear canal of the ear of the second test subject. Optionally, the support element can be moved (e.g., bent) to fit the apparatus 10 for the second user. In some optional aspects, the elongate body can be moved to a second position of the plurality of positions. In this way, the apparatus 10 can be adapted for use with different users.

In some aspects, the apparatus can be placed at the left ear of the user. In further aspects, the apparatus can be placed at the right ear of the user. Accordingly, in some aspects, the apparatus 10 can be configured for unilateral stimulation (e.g., stimulation of an ear canal on only one side of the user). In still further aspects, a respective apparatus 10 can be positioned at each ear. In these aspects, it is contemplated that bilateral stimulation (e.g., either alternating or simultaneous stimulation at both car canals) can be performed.

In further aspects, referring to FIG. 16A-16B, in another exemplary embodiment of the apparatus 10, the housing 30 can comprise a first body 50 that is configured to couple to a support element 34. Optionally, the first body 50 can be annular or ring-shaped, or define a portion of a ring. The first body 50 can define a central opening and one or more (outer) openings 52 (e.g., optionally, elongate slots) that are configured to receive a strap or band 70 (FIG. 16B). Although described as openings 52, it is contemplated that the first body 50 can comprise any fastener that is capable of selective engagement with a strap or band 70 as disclosed herein. The strap or band 70 can optionally be a conventional headphone strap or band. For example, the strap or band 70 can be configured to go over the head of the user or around the back of the head/neck and over the cars in the manner of conventional audio headphones. Said strap or band 70 can be configured to engage the head, the neck, or one or both ears of the user to position and support the housing relative to the user. In further aspects, the strap or band 70 can be configured to extend around and rest on at least a portion of the outer ear. In some aspects, the strap or band 70 can be a rigid band. In further aspects, the strap or band 70 can be a semi-rigid, resilient band that can, for example, conform to the shape of the head of the user or the spacing between the ears. In some aspects, the first body 50 can have a perimeter and a plurality of openings 52 (e.g., optionally, five openings) spaced around the perimeter. In this way, the strap can couple to the first body 50 in a plurality of angular orientations, based on the opening(s) 52 to which the strap couples. Alternatively, it is contemplated that the first body 50 can comprise a plurality of fasteners spaced around the perimeter of the first body, with each fastener configured to engage the strap at a respective angular orientation.

The first body 52 of the housing 30 can couple to a second body 54 so that the second body 54 is pivotable relative to the first body about a first pivot axis 56. Optionally, the second body 54 can be annular or have a ring shape that defines a central opening. The housing 30 can further comprise a third body 58 that is pivotably coupled to the second body about a second pivot axis 60. Optionally, the first and second pivot axes 56, 60 can be on opposing sides 61 of the third body 58. In exemplary aspects, it is contemplated that the first and second pivot axes 56, 60 can be parallel or substantially parallel to one another. In these aspects, and as shown in FIG. 16A, it is contemplated that during use, the third body 58 can be positioned between the first and second pivot axes 56, 60. In exemplary aspects, in a use position, the second body 54 can be positioned outwardly of the first body 50 such that the second body 54 can pivot outwardly (away) from the first body (and the car of the subject).

The third body 58 can define the socket 36 that receives the ball 38 that enables orientation adjustment of the elongate body 12 relative to the housing. It is further contemplated that the third body 58 can overlie or be positioned within the respective central openings defined by the first body 50 and the second body 54, thereby allowing for positioning of the electrodes 20, 22 relative to the ear of the subject (through the central openings of the first body and the second body as shown in FIG. 16A). In some exemplary aspects, it is contemplated that the first body 50 can have an operative height that is greater than an operative height of the second body 54, and the operative height of the second body can be greater than an operative height of the third body 58. Therefore, when the second body 54 is pivoted towards the first body 50, the central opening of the second body can overlie a portion of the central opening of the first body. Similarly, when the third body 58 is pivoted towards the second body 54, the third body can overlie the central opening of the second body (and the portion of the central opening of the first body).

In use, the third body 58 can be moved relative to the first body 50 via adjustment (e.g., pivotal movement) of the second body 54 about the first and/or second pivot axes 56, 60 and/or by adjustment (e.g., pivotal movement) of the third body about the second pivot axis 60. For example, the second body 54 can pivot toward or away from the first body 50, and the third body 58 can be pivoted toward or away from the second body, thereby allowing the third body to be shifted or angled relative to the car of the user in any desirable orientation. As shown in comparing FIGS. 16C and 16D, the third body 58 can be shifted outwardly from the ear (FIG. 16D), thereby moving the probe away from the car or moved toward the ear (FIG. 16C) (e.g., to position the first electrode 20 deeper into the ear canal). In this way, the first and second electrodes 20, 22 can be comfortably positioned at the ear of the user.

Referring also to FIG. 16B, in some optional aspects, the strap, band, or other support element 34 (e.g., the strap or band 70) can extend between both ears, and a respective housing 30 can be positioned at each ear, with each housing supporting first and second electrodes 20, 22. In this way, simultaneous or alternating stimulation of each ear can be achieved.

Referring also to FIG. 17, a system 100 can comprise an apparatus 10 and a stimulation generator 102. The stimulation generator 102 can be in communication with the first electrical conductor 24 and the second electrical conductor 26 of the apparatus 10. The stimulation generator 102 can be configured to generate current for providing electrical stimulation through or between the first and second electrodes 20, 22 of the apparatus 10.

Optionally, the system 100 can comprise a computing device (e.g., computing device 1001 as further disclosed herein). The computing device can comprise at one or more processors (e.g., processor 1003) and a memory (e.g., mass storage device 1004) in communication with the processor(s). The memory can comprise instructions that, when executed by the processor(s), causes the processor(s) to receive data from the apparatus 10. The computing device can further comprise a display device (e.g., display device 1011) and an input device (e.g., input device 1020). The memory can comprise instructions that, when executed by the processor(s), causes the processor(s) to cause the display device to display the data received from the apparatus. In yet further aspects, the computing device can receive an input from a clinician to enable the clinician to adjust one or more parameters of the stimulation generator (e.g., pulse frequency, pulse amplitude, pulse width, or duration of a stimulation session) based on the received data.

In further aspects, memory can comprise instructions that, when executed by the processor(s), causes the processor(s) to automatically adjust the one or more parameters of the stimulation generator based on the received data from the apparatus 10.

E. Computing Device

FIG. 18 shows a computing system 1000 including an exemplary configuration of a computing device 1001 for use with the stimulation system 100. In some aspects, the computing device 1001 can be part of a network. In further aspects, it is contemplated that a separate computing device, such as, for example, a tablet, laptop, or desktop computer can communicate with the system 10 and can enable the operator to interface with the system 10.

The computing device 1001 may comprise one or more processors 1003, a system memory 1012, and a bus 1013 that couples various components of the computing device 1001 including the one or more processors 1003 to the system memory 1012. In the case of multiple processors 1003, the computing device 1001 may utilize parallel computing.

The bus 1013 may comprise one or more of several possible types of bus structures, such as a memory bus, memory controller, a peripheral bus, an accelerated graphics port, and a processor or local bus using any of a variety of bus architectures.

The computing device 1001 may operate on and/or comprise a variety of computer readable media (e.g., non-transitory). Computer readable media may be any available media that is accessible by the computing device 1001 and comprises, non-transitory, volatile and/or non-volatile media, removable and non-removable media. The system memory 1012 has computer readable media in the form of volatile memory, such as random access memory (RAM), and/or non-volatile memory, such as read only memory (ROM). The system memory 1012 may store data such as apparatus data 1007 (i.e., data from signals received by the electrodes) and/or program modules such as operating system 1005 and stimulation routine software 1006 that are accessible to and/or are operated on by the one or more processors 1003.

The computing device 1001 may also comprise other removable/non-removable, volatile/non-volatile computer storage media. The mass storage device 1004 may provide non-volatile storage of computer code, computer readable instructions, data structures, program modules, and other data for the computing device 1001. The mass storage device 1004 may be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules may be stored on the mass storage device 1004. An operating system 1005 and stimulation routine software 1006 may be stored on the mass storage device 1004. One or more of the operating system 1005 and stimulation routine software 1006 (or some combination thereof) may comprise program modules and the stimulation routine software 1006. The apparatus data 1007 may also be stored on the mass storage device 1004. The apparatus data 1007 may be stored in any of one or more databases known in the art. The databases may be centralized or distributed across multiple locations within the network 1015.

A user may enter commands and information into the computing device 1001 using an input device 1020. Such input devices comprise, but are not limited to, a keyboard, pointing device (e.g., a computer mouse, remote control), a microphone, a joystick, a scanner, tactile input devices such as gloves, and other body coverings, motion sensor, and the like. These and other input devices may be connected to the one or more processors 1003 using a human machine interface 1002 that is coupled to the bus 1013, but may be connected by other interface and bus structures, such as a parallel port, game port, an IEEE 1394 Port (also known as a Firewire port), a serial port, network adapter 1008, and/or a universal serial bus (USB).

A display device 1011 may also be connected to the bus 1013 using an interface, such as a display adapter 1009. It is contemplated that the computing device 1001 may have more than one display adapter 1009 and the computing device 1001 may have more than one display device 1011. A display device 1011 may be a monitor, an LCD (Liquid Crystal Display), light emitting diode (LED) display, television, smart lens, smart glass, and/ or a projector. In addition to the display device 1011, other output peripheral devices may comprise components such as speakers (not shown) and a printer (not shown) which may be connected to the computing device 1001 using Input/Output Interface 1010. Any step and/or result of the methods may be output (or caused to be output) in any form to an output device. Such output may be any form of visual representation, including, but not limited to, textual, graphical, animation, audio, tactile, and the like. The display device 1011 and computing device 1001 may be part of one device, or separate devices.

The computing device 1001 may operate in a networked environment using logical connections to one or more remote computing devices 1014*a,b,c*. A remote computing device 1014*a,b,c* may be a personal computer, computing station (e.g., workstation), portable computer (e.g., laptop, mobile phone, tablet device), smart device (e.g., smartphone, smart watch, activity tracker, smart apparel, smart accessory), security and/or monitoring device, a server, a router, a network computer, a peer device, edge device or other common network node, and so on. Logical connections between the computing device 1001 and a remote computing device 1014*a,b,c* may be made using a network 1015, such as a local area network (LAN) and/or a general wide area network (WAN), or a Cloud-based network. Such network connections may be through a network adapter 1008. A network adapter 1008 may be implemented in both wired and wireless environments. Such networking environments are conventional and commonplace in dwellings, offices, enterprise-wide computer networks, intranets, and the Internet. It is contemplated that the remote computing devices 1014*a,b,c* can optionally have some or all of the components disclosed as being part of computing device 1001. In various further aspects, it is contemplated that some or all aspects of data processing described herein can be performed via cloud computing on one or more servers or other remote computing devices. Accordingly, at least a portion of the system 1000 can be configured with internet connectivity.

E. Track and Map Responses

In some aspects, the system described herein can be used when tracking and mapping user responses. For example, a system can be configured to provide VNS only during specific durations, such as, for example, when a user is performing a desired task.

Such tracking and mapping of user responses can be beneficial for analyzing efficacy in users such as stroke survivors. For example, a computing device can receive feedback such as, for example, a force applied to a force sensor. A user can be instructed (e.g., via a display device) to apply a select force, within maximum and minimum thresholds. The computing device can, based on the feedback from the force sensor, whether the user applied the select force within the thresholds for a predetermined duration and, in response, provide VNS (e.g., via the system 100). Similar VNS delivery based on a tracked metric can be used for PTSD treatment or other diseases or disorders.

F. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example, disclosed arc kits for stimulating the auricular vagus nerve, the kit comprising a device for positioning in the inner ear that delivers electrical pulses. Disclosed are kits for stimulating the auricular vagus nerve, the kit comprising an electrode wrapped in or treated with conductive material with instructions for placement in the external ear of a subject and for delivering electrical pulses to a subject. Optionally, the electrode can be provided as a component of an apparatus 10 as disclosed herein.

In further aspects, a kit can comprise a plurality of apparatuses 10, wherein each apparatus of the plurality of apparatuses differs from the other of the plurality of apparatuses by at least one of: a spacing between the first electrode and the second electrode, a dimension of the first electrode, a dimension of the second electrode, a shape of the first electrode, or a shape of the second electrode.

Examples

1. BACKGROUND

Vagus nerve stimulation (VNS) is FDA approved for treatment of depression and epilepsy. Human trials are examining its therapeutic potential in multiple chronic inflammatory disorders including, but not limited to fibromyalgia, migraine headaches, and obesity. Preclinical animal work is also showing promise for treating psychiatric disorders such as post-traumatic stress disorder and motor impairments resulting from neurological injury to the corticospinal tract. In post-traumatic stress disorder, exposure therapy works to extinguish conditioned fears through repeated reminders of traumatic events. Extinction of the conditioned fear depends on the consolidation of new memories made with these exposures. VNS is being explored as an adjunct therapy to improve consolidation and maintenance of the extinction memory. The idea is that under stressful conditions, the vagus nerve signals the brain to facilitate the storage of new memories while, as part of the parasympathetic nervous system, it slows the sympathetic response.

Traumatic events lead to activation of the sympathetic nervous system via the fight-or-flight response. The resulting peripheral changes, such as increased heart and respiration rate, occur during the memory consolidation window and are associated with enhanced memory storage. However, epinephrine does not readily cross the blood-brain barrier. Rather, it binds to beta-adrenergic receptors on the vagus nerve, which then activate brainstem nuclei to release norepinephrine throughout the brain, leading to storage of a newly acquired memory. VNS promotes brain plasticity but bypasses the peripheral fight-or-flight response. Rather, VNS engages the parasympathetic nervous system, slowing heart rate and increasing gut motility. Therefore, pairing VNS with exposure therapy has the potential to strengthen the extinction memory by tapping into mechanisms that enhance storage of the traumatic memory without the requirement of a sympathetic stress response Preclinical animal work is providing support for this theory (FIG. 1). In fear conditioned rats undergoing extinction training, VNS is temporally paired with exposures to a conditioned stimulus (ie, an auditory tone previously paired with electrical shocks to the limb).

Figure 1A:
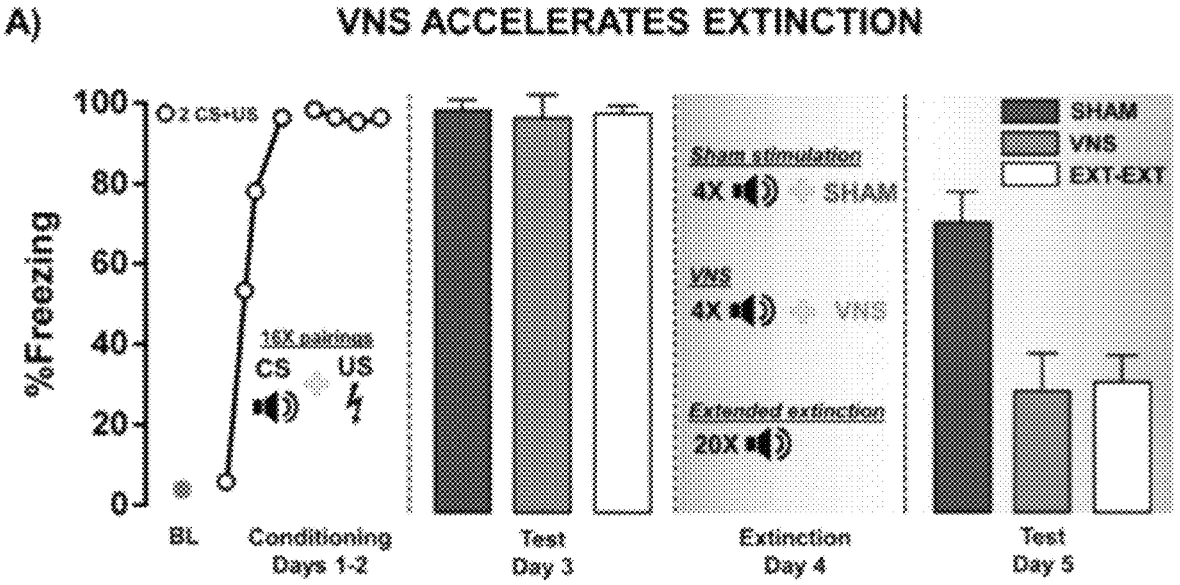
FIG. 1A and FIG. 1B show an example of the effects of vagus nerve stimulation (VNS) during extinction training.

As shown in the FIG. 1A, following auditory fear conditioning, rats showed similar levels of freezing. On the following day, tones were paired with either VNS or sham stimulation, and 20 tones sounded alone in another group to facilitate extended extinction. Results showed that the VNS-treated group exhibited superior extinction to the sham-treated group and equivalent extinction to the group that were exposed to 5 times more tones during extinction training, indicating that VNS accelerates extinction.

Figure 1B:
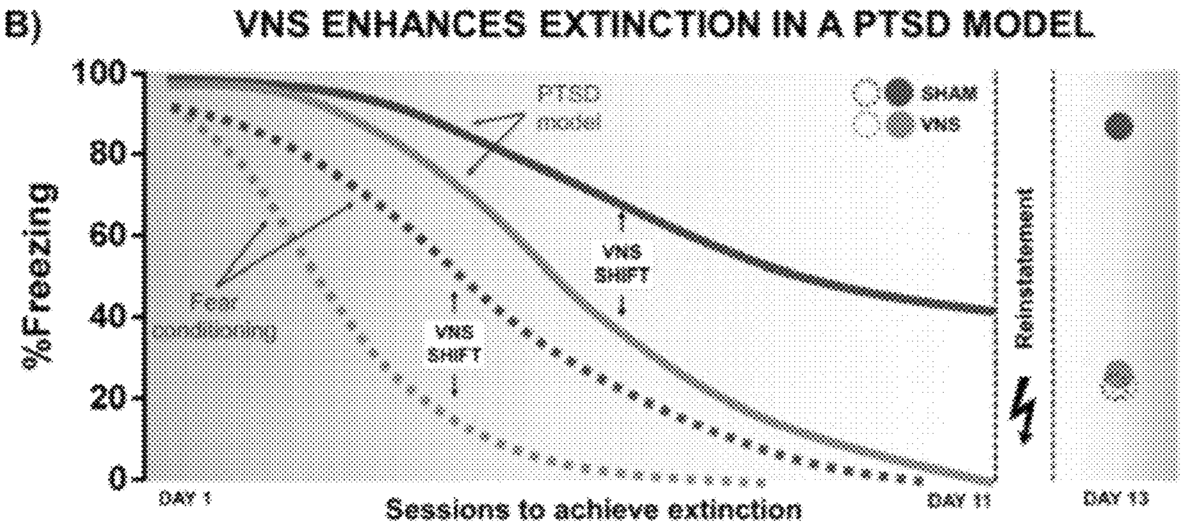

A more recent study used a PTSD model, which involves presentation of a more stressful stimulus relative to that from auditory fear conditioning. Following 11 consecutive days of training, five of which were paired with either VNS or sham stimulation, only the VNS-treated group reached remission of fear, freezing on less than 10% of conditioned stimulus presentations (FIG. 1B). VNS-treated rats also showed no reinstatement of fear when tested 2 weeks later.

Figure 2A:
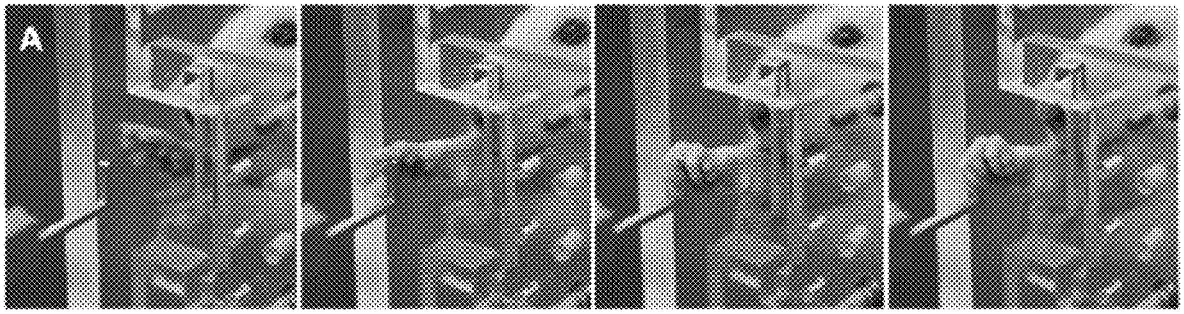
FIG. 2A and FIG. 2B show an exemplary motor training paradigm used in rodent studies to evaluate the effects of VNS to enhance rehabilitation outcomes after damage to the corticospinal tract.
Figure 2B:
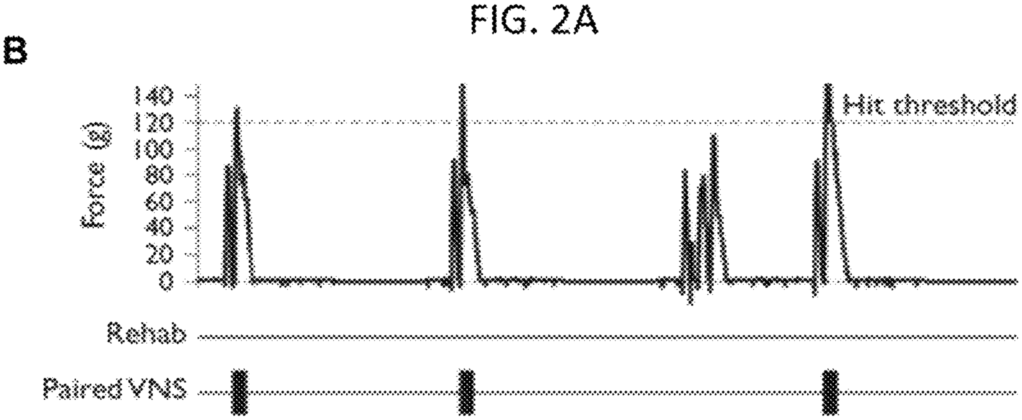

VNS is also being explored as an adjunct to treat movement impairments that result from neurological injury to the corticospinal system, such as with stroke or spinal cord injury. Similar to PTSD, the theoretical mechanism of action is increased noradrenergic activity in the brain which enhances memory consolidation during motor re-learning. A paradigm used in several rodent studies involves training the rat to pull on a strain gauge before lesioning the corticospinal tract (FIG. 2). Re-emphasizing the importance of pairing VNS with behavioral or environmental events, these studies often involve a target force that the paretic limb must achieve in order for VNS to be administered. The objective is to reinforce patterns of cortical activation that produce proficient motor output from the paretic limb.

Figure 3A:
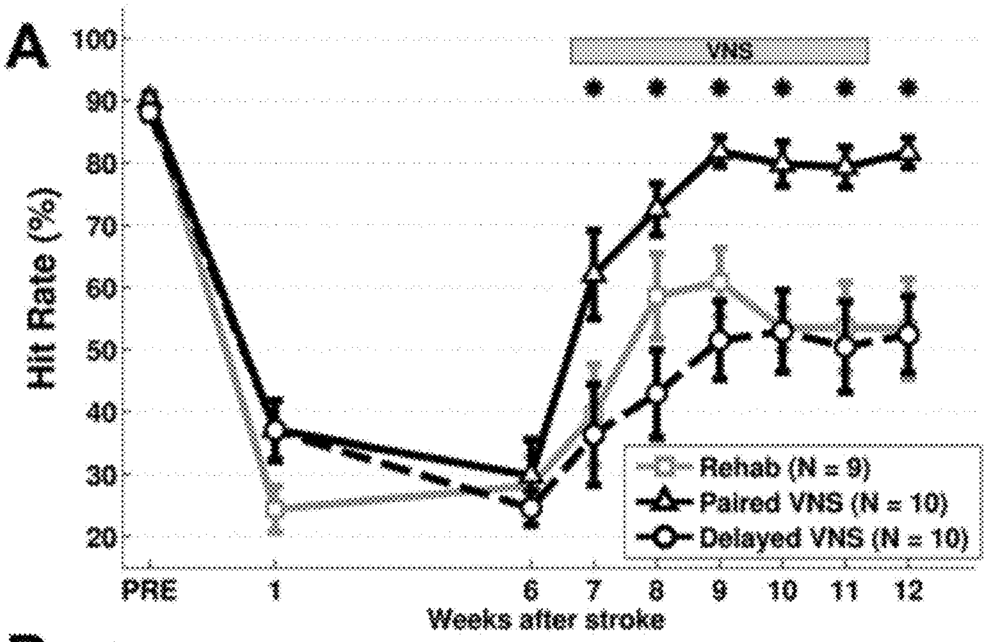
FIG. 3A and FIG. 3B show an example of the effects of VNS during motor retraining after stroke. Both
Figure 3B:
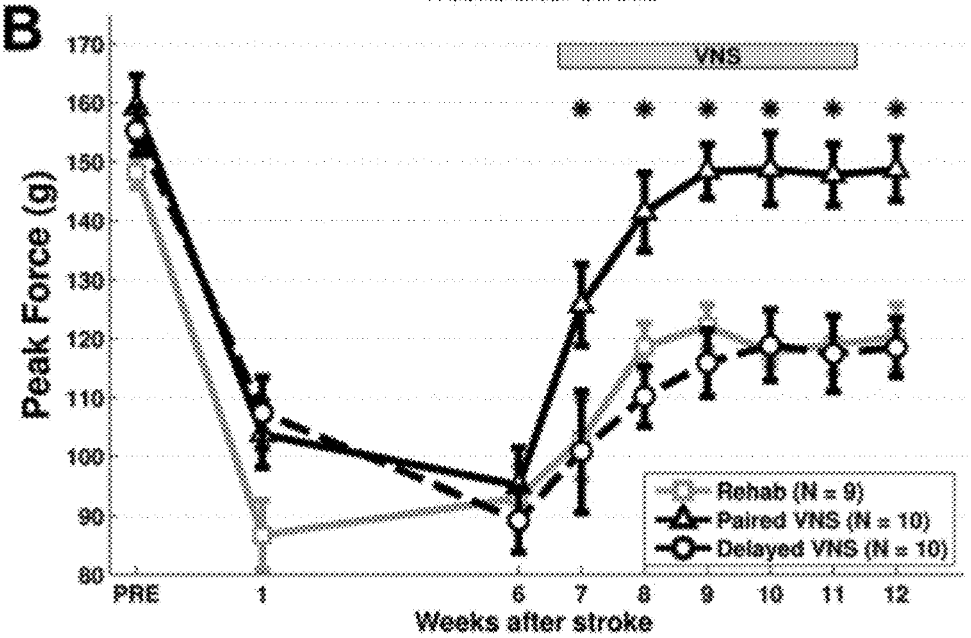

An accumulation of evidence from these animal studies demonstrates that pairing VNS with motor retraining leads to superior improvements in motor function when compared to motor retraining alone. Results of the study shown in FIG. 3 reinforce the importance of the temporal coincidence of pairing stimulation with behavior or environmental events, as another group that received delayed VNS does not exhibit the same degree of improved motor function.

Figure 4:
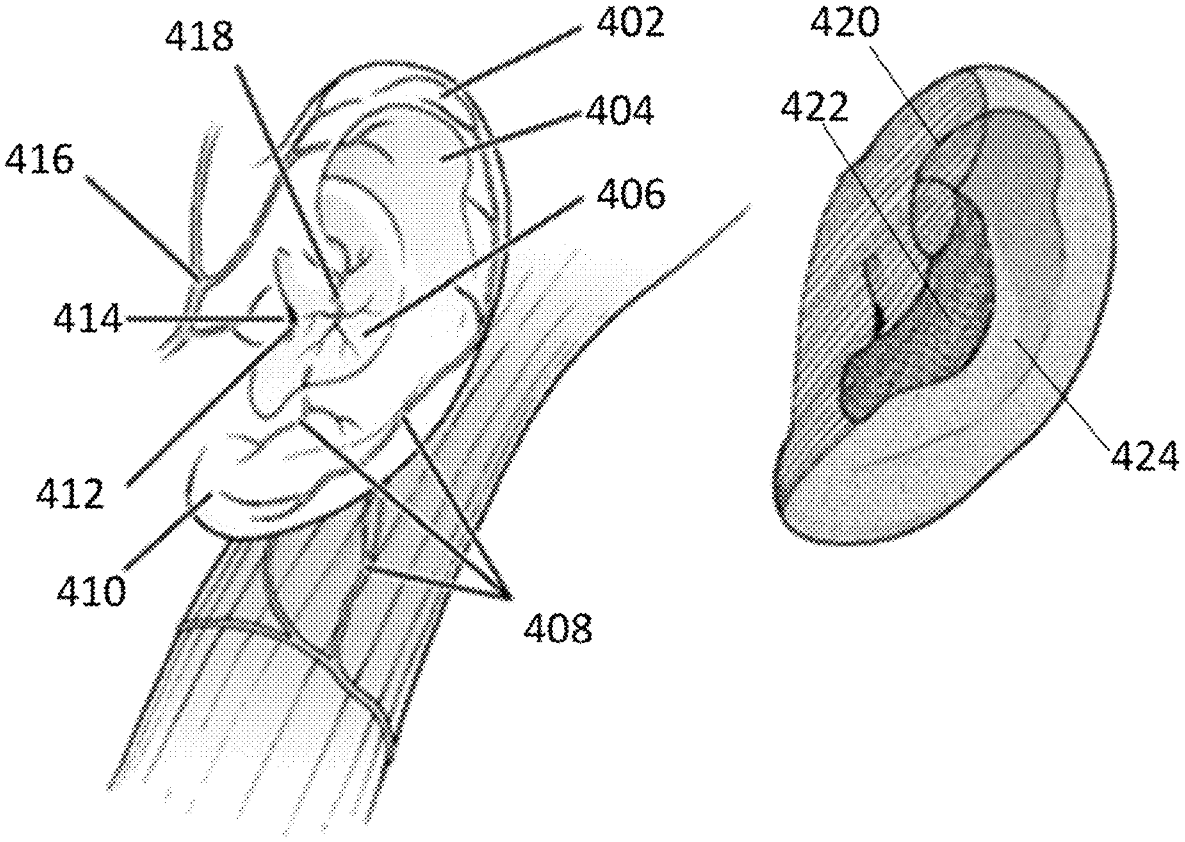
FIG. 4 shows afferent innervation from the auricular branch of the vagus nerve in the external ear.

In light of preclinical findings, a number of implantable stimulators have been developed and are currently on the market. These devices have some drawbacks such as the need to undergo a surgical procedure that is both expensive and not reimbursed by most insurances. Such factors have led to the development of devices that seek to recruit the vagus nerve noninvasively through transcutaneous stimulation. A noninvasive approach to VNS appears plausible given human cadaver evidence of dense innervation in the ear from the auricular branch of the vagus nerve (FIG. 4). As shown in FIG. 4, the car can have a helix 402, an antihelix 404, a concha 406, a great auricular nerve 408, a lobule 410, an external auditory meatus 412, a tragus 414, an auriculotermporal nerve 416, and an auricular branch of the vagus nerve 418. The car can have a first portion 420 associated with the auriculotemporal nerve, a second portion 422 associated with the auricular branch of the vagus nerve, and a third portion 424 associated with the great auricular nerve. A growing number of published studies have reported promising treatment effects, but there is no evidence that auricular stimulation activates the noradrenergic mechanisms thought to underlie the therapeutic benefits of VNS. In fact, there are several published reports of null findings from auricular stimulation on changes in pupil diameter, which is an established biomarker of noradrenergic activation. This is problematic in that pairing activation of the noradrenergic system with behavioral and/or environmental events appears to be a critical determinant of treatment effects. Without verification that the system is engaged, it is impossible to ensure the incidence of nor the temporal coincidence of activation with external events.

2. METHOD

The noradrenergic system can be activated via transcutaneous stimulation of the external ear. As further disclosed herein, a device can be developed to replicate electrode placement and stimulation parameters in a form factor for use in clinical and research settings. Pulse waveforms are generated by custom software and output by a commercially-available, isolated bipolar constant current stimulator (DSS, Digitimer Ltd, UK). Electrical current is controlled via custom software and a data acquisition device. Pulse trains consist of symmetric, biphasic waveforms with prespecified amplitudes tailored to the individual subject. Pulse width, frequency and overall train duration is fixed.

To verify noradrenergic activation, recordings of pupil dilation were obtained from 19 neurologically-intact adults. Modulation of pupil diameter is an established biomarker of the noradrenergic system. A three-part experimental procedure is carried out to 1) configure hardware/software and apply electrode interface, 2) establish perceptual threshold, and 3) to measure changes in pupil diameter resulting from stimulation.

First, the skin overlying the targeted landmark on the ear is lightly abraded and cleansed with preparation gel. For canal stimulation, an electrode made from a steel cannula (1.2 cm length, 4 mm diameter) fused to a snap electrode lead with an epoxy material is wrapped in hydrogel and coated in conductive gel. The electrode is inserted into the left ear canal for unilateral stimulation. For concha stimulation, Ag—AgCl disc electrodes (4-mm diameter) are either embedded in a silicone putty or taped on the skin overlying the cymba (anode) and cavum (cathode). These disc electrodes also are used for ear lobe stimulation (sham), with the anode placed approximately 5 mm anterior to the cathode.

Next, the subject undergoes a 0.1 mA-up/0.3 mA-down staircase procedure to establish perceptual thresholds, determining the minimum electrical current needed to evoke a percept. Perceptual threshold is taken as the average amplitude after eight reversals. The subject is instructed to raise his/her left hand when stimulation is perceived at the targeted location on the external ear. Two thresholding procedures are administered for reliability purposes, and the average of the two is taken as the perceptual threshold to calculate electrical current amplitudes entered into a custom program controlling the stimulating device during eye tracking procedures. Perceptual threshold is established for a given combination of stimulation parameters prior to eye tracking procedures.

Then, saccades and pupil diameter are recorded (500 Hz sample rate) continuously while a series of visual cues configured in software native to a commercially available eye tracking system are presented on a computer monitor (FIG. 5A). Visual cues serve to provide instruction to the participant. The head and chin of the subject are positioned in a mounted frame, and room lights are turned off while measurements are obtained. Following a calibration procedure, the computer monitor background de-illuminates for 10 s to allow the participant an opportunity to close and/or relax their eyes. The background of the monitor illuminates immediately thereafter, at which time the participant minimizes blinks but is able to gaze freely. A fixation cross is presented on the monitor at 5 s, cueing the participant to orient gaze to the cross and avoid blinking entirely. The color of the cross changes from red to green at 6 s, signaling the participant to maintain fixation on the center of the cross until it disappears from the monitor at 10 s. Saccades alter pupil diameter so fixation is necessary to dissociate the effects of stimulation on pupil diameter. Pulse trains are administered 400 ms after the cross changes color from red to green (i.e., 6.4 s). To minimize transient effects of stimuli that are possible in pupillometry, a ~9-second interval elapses between single stimulation trains. A series of consecutive trials are recorded before the monitor background de-illuminates again to allow the participant an opportunity to rest their eyes, resulting in one block of testing. A given combination of stimulation parameters is administered on an equal number of trials in random order within each testing block. A pre-specified number of testing blocks are administered before the participant is able to withdraw their head from the frame, resulting in a complete set of testing. This procedure is repeated to test the effects of stimulation to different locations and/or combinations of stimulation parameters at a given location. To minimize the potential for carryover effects, a 10-minute rest period is taken between sets.

Figures 6A, 6B:
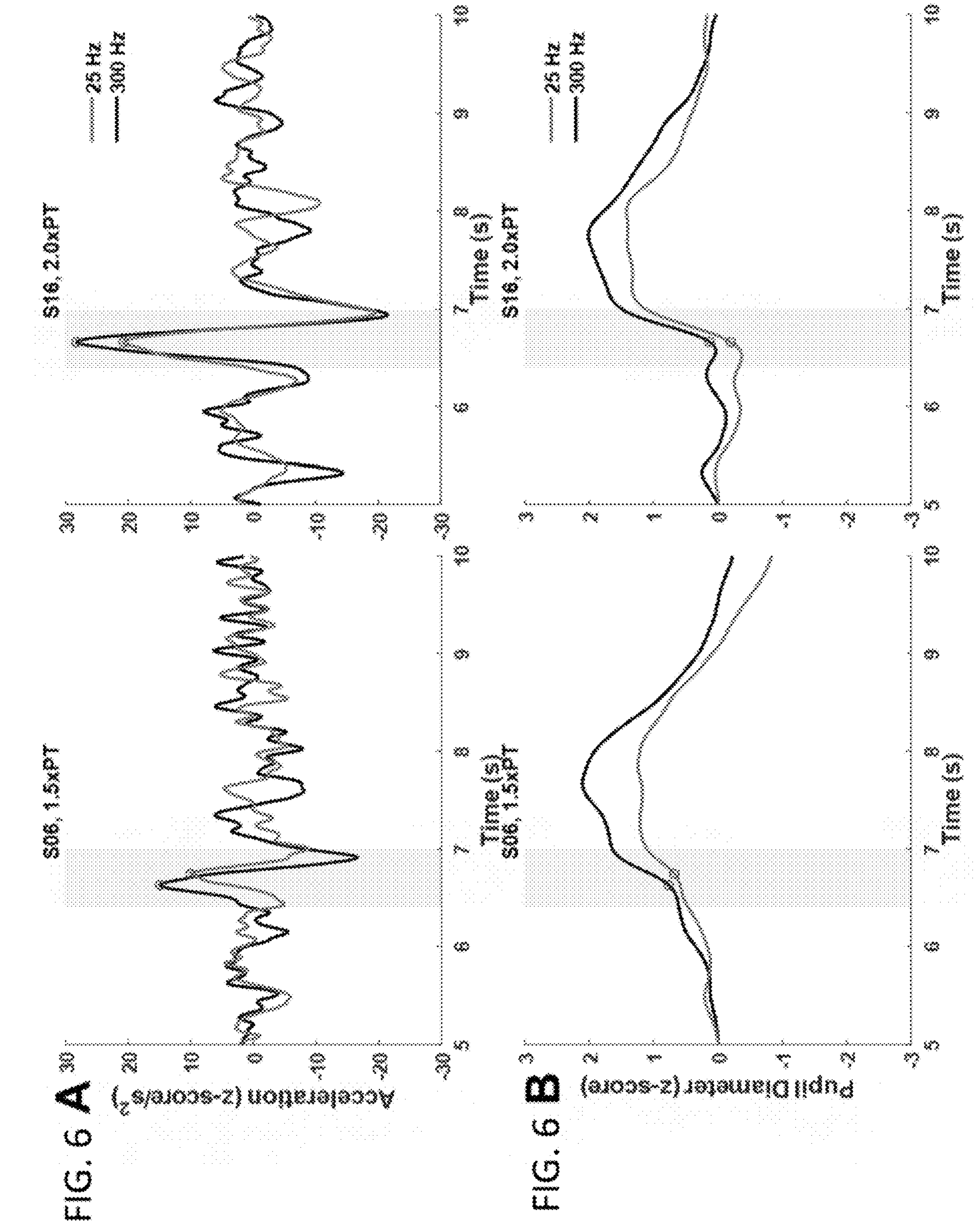
FIG. 6A and FIG. 6B are studies on pupil diameter.

In accordance with standard data processing guidelines for pupillometry, all pupillary responses features are calculated from the waveform average of all pulse trains administered at a given location and fixed combination of stimulation parameters. FIG. 5B shows a representative waveform-averaged pupillary response depicting different features that represent the timing and size of the response. For response timing, the magnitude and latency of the peak positive acceleration within the stimulation epoch (6.4-7.05 s) is used to index response onset (FIGS. 6A & B). Latency of peak dilation is measured between the time of peak acceleration and 1.6 s after stimulation onset (6.4-8 s). For response size, the change in pupil diameter between the time of peak acceleration and peak dilation is quantified. Since the time course to peak dilation can vary and be more or less sustained depending on how pulse trains influence postsynaptic firing in locus coeruleus, area under the curve (AuC) is quantified between the times of peak acceleration and peak dilation.

3. RESULTS

Shown in FIG. 7A is the change in pupil diameter in the sample of subjects resulting from pulse trains applied at each location on the external ear. A clear modulation is evident for pulse amplitudes at and above perceptual threshold, particularly for the canal relative to other locations. Shown in FIG. 7B are waveform averaged responses elicited by pulse trains applied to each location from a representative subject with pulse amplitudes at and above perceptual threshold. Note that activation of nociceptors mediating pain perception can engage an autonomic response that dilates the pupil. Determining whether the vagus nerve is recruited via a noninvasive approach in humans is not straightforward because the vagus nerve is composed of A, B, and C fiber types. To determine if nociceptors were involved in mediating responses, subjects were asked to report any instance of pain. Of the 19 subjects tested, one reported mild dizziness at the 2.0×PT amplitude. There were no reports of pain or discomfort.

Shown in FIGS. 8A & B are the effects of pulse frequency on metrics of pupillary response size and timing. AuC modulated with pulse frequency, but effects were contingent on location and pulse amplitude. Targeting the canal with higher pulse frequency, in particular, tended to elicit stronger pupillary responses (FIG. 8A). Higher pulse frequency reduced the latencies of peak acceleration and peak dilation of pupil diameter, thus, decreasing time elapsing between stimulation and the onset and peak of pupillary responses (FIG. 8B).

Inspection of pupil diameter recordings from individual pulse trains revealed instances with strong and abrupt modulations in pupil diameter shortly after the time of stimulation onset. A 0.0×PT pulse amplitude was randomized into each block of trials, serving as a reference of noradrenergic activity during eye tracking procedures, which is likely influenced by both tonic and phasic firing of locus coeruleus. Accepted standards for characterizing pupillary responses at the trial level have not been defined. The incidence of pupillary responses from individual pulse trains in the present study, therefore, was estimated by calculating the percentage of trials where the peak positive acceleration during the stimulation epoch and subsequent peak dilation nominally exceeded both features when the 0.0×PT pulse amplitude was applied. Based on these criteria, pupillary responses were elicited by single pulse trains. Shown in FIGS. 9A & B are recordings of pupil diameter from single pulse trains at different pulse frequencies (rows) and amplitudes (columns) in a subject.

4. CONCLUSION

The findings indicate that the taVNS interface used in these experiments produces an acute autonomic response. The magnitude and timing of effects in absence of pain percepts point to activation of the noradrenergic system, which is thought to contribute to the adaptive effects of both invasive and noninvasive forms of VNS. Changes in the efficiency of central synapses are thought to underlie learning, and norepinephrine is known to regulate synaptic function. Modulating aspects of physiology underlying attentional control and memory formation on an acute basis as shown here, therefore, enhances the potential for applications to support (re)learning, as it may enable activation of these physiological mechanisms to be synchronized with behavioral, environmental, or task-related events.

5. STIMULATION OF DIFFERENT PORTIONS OF EAR CANAL

FIGS. 19A-B show waveform-averaged pupil diameter recordings when stimulating on the superior wall of each canal wall in two subjects at a fixed stimulation amplitude (S01=1.35 mA, S02=1.275 mA) and frequency (300 Hz).

FIGS. 19C-D show waveform-averaged pupil diameter recordings when stimulating on the anterior wall of each canal wall in two subjects at a fixed stimulation amplitude (S01=1.35 mA, S02=1.275 mA) and frequency (300 Hz). FIGS. 19E-F show waveform-averaged pupil diameter recordings when stimulating on the inferior wall of each canal wall in two subjects at a fixed stimulation amplitude (S01=1.35 mA, SO2=1.275 mA) and frequency (300 Hz). FIGS. 19G-H show waveform-averaged pupil diameter recordings when stimulating on the posterior wall of each canal wall in two subjects at a fixed stimulation amplitude (S01=1.35 mA, S02=1.275 mA) and frequency (300 Hz). Solid lines correspond to pupil diameter (left vertical axis) with (black trace) and without (gray trace) stimulation. Dashed lines correspond to acceleration of pupil diameter (right vertical axis) with (black trace) and without (gray trace) stimulation. Circles connote times of peak positive acceleration, and shaded region connotes stimulation epoch.

Variability in the size of pupillary responses elicited by stimulation on each wall within an individual subject can be noted. Also note variability in the size of pupillary responses elicited by stimulation on each wall between both subjects can be noted. Subject S01 (FIGS. 19A,C,E,G) exhibits the strongest pupillary response with stimulation applied to anterior and posterior walls, whereas, Subject S02 (FIGS. 19B,D,F,H) exhibits the strongest response with stimulation applied to the inferior wall. Acknowledging the intra- and inter-subject variability that exists, these data demonstrate that a device capable of more focal application of electrical current selectively targeting each canal wall can drive differential activation of noradrenergic mechanisms that may be tailored to individual human subjects.

Exemplary Aspects

In view of the described device, systems, and methods and variations thereof, herein below are certain more particularly described aspects of the invention. These particularly recited aspects should not, however, be interpreted to have any limiting effect on any different claims containing different or more general teachings described herein, or that the "particular" aspects are somehow limited in some way other than the inherent meanings of the language literally used therein.

Aspect 1: An apparatus comprising:

an elongate body having a longitudinal axis and a first end and a second end that are spaced along the longitudinal axis;

a first electrode positioned at the first end of the elongate body, wherein the first electrode is configured to be received at least partially in an ear canal of an ear;

a second electrode positioned between the first electrode and the second end of the elongate body;

a first conductor in electrical communication with the first electrode;

a second conductor in electrical communication with the second electrode; and a housing that receives a portion of the elongate body therein, wherein the housing has a central axis, wherein the elongate body is pivotable relative to the housing about the central axis, wherein the housing is configured to retain the elongate body in a plurality of positions that are offset from each other by at least an azimuthal angle offset, wherein the apparatus is configured to provide electrical stimulation through or between the first and second electrodes, and wherein the housing comprises a support element that is configured to support the apparatus on an outer ear portion of the ear to permit electrical stimulation of a nerve adjacent to or within the ear.

Aspect 2: The apparatus of aspect 1, wherein the housing defines a socket, wherein the apparatus further comprises a ball having an outer surface that is pivotably received within the socket, wherein the ball is fixedly coupled to the elongate body so that the ball and the socket cooperate to enable movement of the elongate body relative to the housing to adjust an azimuthal angle and a polar angle of the elongate body relative to the central axis of the housing.

Aspect 3: The apparatus of aspect 1 or aspect 2, wherein each of the first electrode and the second electrode circumferentially surrounds and extends radially outwardly from a respective portion of the elongate body.

Aspect 4: The apparatus of any one of the preceding aspects, wherein the second electrode has an outer surface that is at least partially spherical.

Aspect 5: The apparatus of aspect 4, wherein the first electrode has an outer surface that is at least partially spherical.

Aspect 6: The apparatus of aspect 4, wherein the first electrode has a non-spherical outer surface.

Aspect 7: The apparatus of any one of the preceding aspects, further comprising a retention structure that is configured to retain the elongate body in at least one position of the plurality of positions.

Aspect 8: The apparatus of any one of the preceding aspects, wherein the retention structure comprises a plurality of detents, wherein a respective detent of the plurality of detents is provided at each of the plurality of positions for retaining the elongate body at the respective position of the plurality of positions.

Aspect 9: The apparatus of aspect 8, wherein the plurality of detents are spaced apart in a circular pattern.

Aspect 10: The apparatus of aspect 8 or aspect 9, wherein the plurality of detents are spaced apart in a non-circular pattern.

Aspect 11: The apparatus of aspect 10, wherein the non-circular pattern is D-shaped.

Aspect 12: The apparatus of any one of aspects 8-11, wherein each detent of the plurality of detents comprises an opening that receives and at least partially surrounds a portion of the elongate body.

Aspect 13: The apparatus of aspect 12, wherein the opening of each detent of the plurality of detents is surrounded by resilient material that is configured to flex to receive the elongate body.

Aspect 14: The apparatus of any one of the preceding aspects, wherein the second end of the elongate body extends from the housing by at least two centimeters.

Aspect 15: The apparatus of any one of the preceding aspects, wherein the support element comprises a strap or band that is configured to engage a head, a neck, or the ear.

Aspect 16: The apparatus of any one of the preceding aspects, wherein the first conductor extends through at least a portion of the elongate body.

Aspect 17: The apparatus of any one of the preceding aspects, wherein the second conductor extends through at least a portion of the elongate body.

Aspect 18: The apparatus of any aspects 2-16, wherein the housing comprises:

a first body;

a second body that is pivotably coupled to the first body about a first pivotal axis; and a third body that is pivotably coupled to the second body about a second pivotal axis, wherein the third body defines the socket.

Aspect 19: The apparatus of aspect 18, wherein the first and second pivotal axes are on opposing ends of the second body.

Aspect 20: The apparatus of aspect 18 or aspect 19, wherein the first body has a perimeter, wherein the first body defines a plurality of openings positioned about the perimeter of the first body, wherein the plurality of openings are configured to couple to the support element.

Aspect 21: A method of acutely activating the noradrenergic system in a subject comprising:

applying one or more electrical pulses to an ear of the subject, wherein the one or more electrical pulses are sufficient to acutely activate the noradrenergic system of the subject, wherein the one or more electrical pulses are applied using an apparatus as in any one of aspects 1-20.

Aspect 22: The method of aspect 21, wherein applying one or more electrical pulses to the ear of the subject comprises:

positioning at least a portion of a device on an outer ear of the ear of the subject; and generating electrical pulses with the device, wherein the electrical pulses are transmitted through the ear to a nerve in the subject.

Aspect 23: The method of aspect 21 or aspect 22, wherein the one or more electrical pulses arc applied unilaterally to the subject.

Aspect 24: The method of aspect 23, wherein the one or more electrical pulses are applied to one of a left car or a right car of the subject.

Aspect 25: The method of aspect 21 or aspect 22, wherein the one or more electrical pulses are applied bilaterally to the subject.

Aspect 26: The method of any one of aspects 21-25, wherein acutely activating the noradrenergic system occurs via stimulation to the nerve.

Aspect 27: The method of any one of aspects 21-26, wherein the nerve is a vagus nerve having an auricular branch, and wherein the electrical pulses are transmitted through the ear to the auricular branch of the vagus nerve.

Aspect 28: The method of any one of aspects 21-27, wherein positioning a device on the car of the subject comprises positioning a cylindrical or spherical electrode wrapped in conductive material or two electrodes treated with a conductive material on the external ear of the subject.

Aspect 29: The method of any one of aspects 21-28, wherein activation of the noradrenergic system is confirmed by assessing pupil dilation.

Aspect 30: The method of aspect 29, wherein assessing pupil dilation comprises:

quantifying baseline pupil dilation; establishing perceptual thresholds; and measuring changes in pupil dilation from baseline after activation of the noradrenergic system.

Aspect 31: The method of any one of aspects 21-30, wherein the one or more electrical pulses are administered at a frequency of between 1 Hz and 10,000 Hz.

Aspect 32: The method of any one of aspects 21-31, wherein applying one or more electrical pulses to an car canal of the subject occurs for a duration of about 1 ms to 30 minutes.

Aspect 33: The method of any one of aspects 21-22, wherein applying one or more electrical pulses to the ear of the subject comprises applying one or more electrical pulses to the left external ear of the subject.

Aspect 34: The method of aspect 33, wherein applying one or more electrical pulses to the left external ear of the subject comprises applying one or more electrical pulses to the left ear canal of the subject.

Aspect 35: A method of treating a disease or disorder in a subject comprising:

applying one or more electrical pulses to an ear of the subject, wherein the one or more electrical pulses are sufficient to acutely activate the noradrenergic system of the subject such that the disease or disorder in the subject is treated, wherein the one or more electrical pulses are applied using an apparatus as in any one of aspects 1-20.

Aspect 36: The method of aspect 35, wherein the one or more electrical pulses are applied unilaterally to a left ear or a right ear of the subject.

Aspect 37: The method of aspect 36, wherein the one or more electrical pulses are applied bilaterally to the subject.

Aspect 38: The method any one of aspects 35-37, wherein applying one or more electrical pulses to a nerve of the subject comprises applying the one or more electrical pulses according to a treatment paradigm.

Aspect 39: The method of aspect 38, wherein the treatment paradigm comprises a train of electrical pulses for a time period of about 1 ms to about 30 minutes as a single dose.

Aspect 40: The method of aspect 38, wherein the treatment paradigm is applied once daily.

Aspect 41: The method of aspect 38, wherein the treatment paradigm is applied at least twice daily.

Aspect 42: The method of aspect 41, wherein each treatment paradigm is applied within 5 minutes of a preceding treatment paradigm.

Aspect 43: The method of aspect 38, wherein the treatment paradigm is applied once a week.

Aspect 44: The method of aspect 38, wherein the treatment paradigm is applied once a month.

Aspect 45: The method of aspect 38, wherein the disease or disorder is a psychiatric disorder, neurologic disorder, or a chronic inflammatory disorder.

Aspect 46: The method of aspect 45, wherein the psychiatric disorder is post-traumatic stress disorder (PTSD), anxiety, depression, schizophrenia, or motor impairments resulting from neurological injury to the corticospinal tract.

Aspect 47: The method of aspect 45, wherein the neurological disorder is epilepsy or paresis.

Aspect 48: The method of aspect 45, wherein the chronic inflammatory disorder is fibromyalgia, migraine headaches, or obesity.

Aspect 49: The method of any one of aspects 35-48, wherein acute activation of the noradrenergic system extinguishes conditioned fears through repeated reminders of traumatic events.

Aspect 50: The method of any one of aspects 35-49, wherein acute activation of the noradrenergic system improves consolidation and maintenance of the extinction memory.

Aspect 51: The method of any one of aspects 35-50, wherein acutely activating the noradrenergic system comprises stimulating the nerve of the subject.

Aspect 52: A method of ameliorating a symptom associated with a psychiatric disorder, neurological disorder, or chronic inflammatory disorder in a subject comprising applying one or more electrical pulses to a left ear canal of the subject with the apparatus as in any one of aspects 1-20, wherein the one or more electrical pulses are sufficient to ameliorate a symptom associated with a psychiatric disorder, neurological disorder, or chronic inflammatory disorder in a subject.

Aspect 53: A system comprising:

an apparatus as in any one of aspects 1-20; and a stimulation generator in communication with the first electrical conductor and the second electrical conductor, wherein the stimulation generator is configured to generate current for providing electrical stimulation through or between the first and second electrodes of the apparatus.

Aspect 54: The system of aspect 53, further comprising:

at least one processor; and memory in communication with the at least one processor, wherein the memory comprises instructions that, when executed by the at least one processor, cause the at least one processor to:

receive data from the apparatus.

Aspect 55: The system of aspect 54, further comprising:

an input device in communication with the at least one processor; and a display device, wherein the memory comprises instructions that, when executed by the at least one processor, cause the at least one processor to:

cause the display device to display the data received from the apparatus; and receive an input from a clinician to enable the clinician to adjust at least one parameter of the stimulation generator based on the received data.

Aspect 56: The system of aspect 55, wherein the memory comprises instructions that, when executed by the at least one processor, cause the at least one processor to automatically adjust at least one parameter of the stimulation generator based on the received data.

Aspect 57: The system of aspect 56, wherein the at least one parameter comprises a stimulation amplitude or a stimulation frequency.

Aspect 58: A kit comprising:

a plurality of apparatuses as in any one of aspects 1-20, wherein each apparatus of the plurality of apparatuses differs from the other of the plurality of apparatuses by at least one of: a spacing between the first electrode and the second electrode, a dimension of the first electrode, a dimension of the second electrode, a shape of the first electrode, or a shape of the second electrode.

Aspect 59: A method of acutely activating the noradrenergic system in a subject comprising applying one or more electrical pulses to an car of the subject, wherein the one or more electrical pulses are sufficient to acutely activate the noradrenergic system of the subject.

Aspect 60: The method of aspect 59, wherein applying one or more electrical pulses to the ear of the subject comprises:

positioning at least a portion of a device on an outer ear of the ear of the subject; and generating electrical pulses with the device, wherein the electrical pulses are transmitted through the ear to a nerve in the subject.

Aspect 61: The method of aspect 59 or aspect 60, wherein the one or more electrical pulses are applied unilaterally to the subject.

Aspect 62: The method of aspects 61, wherein the one or more electrical pulses are applied to one of a left ear or a right ear of the subject.

Aspect 63: The method of aspects 59 or aspect 60, wherein the one or more electrical pulses are applied bilaterally to the subject.

Aspect 64: The method of any one of aspects 59-63, wherein acutely activating the noradrenergic system occurs via stimulation to the nerve.

Aspect 65: The method of any one of aspects 59-64, wherein the nerve is a vagus nerve having an auricular branch, and wherein the electrical pulses arc transmitted through the ear to the auricular branch of the vagus nerve.

Aspect 66: The method of any one of aspects 59-65, wherein positioning a device on the car of the subject comprises positioning a cylindrical or spherical electrode wrapped in conductive material or two electrodes treated with a conductive material on the external ear of the subject.

Aspect 67: The method of any one of aspects 59-67, wherein activation of the noradrenergic system is confirmed by assessing pupil dilation.

Aspect 68: The method of aspect 67, wherein assessing pupil dilation comprises:

quantifying baseline pupil dilation;

establishing perceptual thresholds; and measuring changes in pupil dilation from baseline after activation of the noradrenergic system.

Aspect 69: The method of any one of aspects 59-64, wherein the one or more electrical pulses are administered at a frequency of between 1 Hz and 10,000 Hz.

Aspect 70: The method any one of aspects 59-64, wherein applying one or more electrical pulses to an ear canal of the subject occurs for a duration of about 1 ms to 1000 ms.

Aspect 71: The method of any one of aspects 59-64, wherein applying one or more electrical pulses to an ear of the subject comprises applying one or more electrical pulses to the left external ear of the subject.

Aspect 72: The method of aspect 71, wherein applying one or more electrical pulses to the left external ear of the subject comprises applying one or more electrical pulses to the left ear canal of the subject.

Aspect 73: A method of treating a disease or disorder in a subject comprising:

applying one or more electrical pulses to at least one of a left ear or a right ear of a subject, wherein the one or more electrical pulses are sufficient to acutely activate the noradrenergic system of the subject such that the disease or disorder in the subject is treated.

Aspect 74: The method of aspect 73, wherein the one or more electrical pulses are applied unilaterally to one car of the subject.

Aspect 75: The method of aspect 74, wherein the one or more electrical pulses are applied simultaneously to both ears of the subject.

Aspect 76: The method of any one of aspects 73-75, wherein applying one or more electrical pulses to a nerve of the subject comprises applying the one or more electrical pulses according to a treatment paradigm.

Aspect 77: The method of aspect 76, wherein the treatment paradigm comprises a train of electrical pulses for a time period of about 1 ms to about 30 minutes as a single dose.

Aspect 78: The method of aspect 76, wherein the treatment paradigm is applied once daily.

Aspect 79: The method of aspect 76, wherein the treatment paradigm is applied at least twice daily.

Aspect 80: The method of aspect 79, wherein each treatment paradigm is applied within 5 minutes of a preceding treatment paradigm.

Aspect 81: The method of aspect 76, wherein the treatment paradigm is applied once a week.

Aspect 82: The method of aspect 76, wherein the treatment paradigm is applied once a month.

Aspect 83: The method of any one of aspects 73-82, wherein the disease or disorder is a psychiatric disorder, neurologic disorder, or a chronic inflammatory disorder.

Aspect 84: The method of aspect 83, wherein the psychiatric disorder is post-traumatic stress disorder (PTSD), anxiety, depression, schizophrenia, or motor impairments resulting from neurological injury to the corticospinal tract.

Aspect 85: The method of aspect 83, wherein the neurological disorder is epilepsy or paresis.

Aspect 86: The method of aspect 83, wherein the chronic inflammatory disorder is fibromyalgia, migraine headaches, or obesity.

Aspect 87: The method of aspect 73, wherein acute activation of the noradrenergic system extinguishes conditioned fears through repeated reminders of traumatic events.

Aspect 88: The method of aspect 73, wherein acute activation of the noradrenergic system improves consolidation and maintenance of the extinction memory.

Aspect 89: The method of aspect 73, wherein acutely activating the noradrenergic system comprises stimulating the nerve of the subject.

Aspect 90: A method of ameliorating a symptom associated with a psychiatric disorder, neurological disorder, or chronic inflammatory disorder in a subject comprising applying one or more electrical pulses to an ear of the subject, wherein the one or more electrical pulses are sufficient to ameliorate a symptom associated with a psychiatric disorder, neurological disorder, or chronic inflammatory disorder in the subject.

Those skilled in the art will recognize, or be able to ascertain using no more than routine experimentation, many equivalents to the specific embodiments of the method and compositions described herein. Such equivalents are intended to be encompassed by the following claims.

The invention claimed is:

1. A method comprising:
- activating a neurotransmitter system of a subject by applying one or more electrical pulses to an ear of a subject to stimulate an auricular branch of a vagus nerve of the subject;
- exposing, simultaneously with the one or more electrical pulses, the subject to an environmental or task-related event for a behavior to be learned;
- measuring, by a pupil measurement device, pupil diameter of the subject over time;
- receiving, by a computing device, the pupil diameter of the subject over time;
- calculating, by the computing device, an area under a curve of data corresponding to the measured pupil diameter over time within a duration between a time of peak acceleration and a time of peak dilation;
- confirming activation of a neurotransmitter system of the subject based on the area under the curve,
- wherein activation of a neurotransmitter system of the subject in combination with exposure to the environmental or task-related event for a behavior to be learned provides a therapeutic benefit to the subject.

2. The method of claim 1, wherein applying one or more electrical pulses to the ear of the subject comprises:
- positioning at least a portion of a device on an outer ear of the ear of the subject; and
- generating electrical pulses with the device, wherein the electrical pulses are transmitted through the ear.

3. The method of claim 1, wherein the one or more electrical pulses are applied unilaterally to the subject.

4. The method of claim 3, wherein the one or more electrical pulses are applied to one of a left ear or a right ear of the subject.

5. The method of claim 1, wherein the one or more electrical pulses are applied bilaterally to the subject.

6. The method of claim 1, wherein applying the one or more electrical pulses to the ear of the subject comprises applying the one or more electrical pulses to an ear canal of the ear.

7. The method of claim 1, wherein applying the one or more electrical pulses to the ear of the subject comprises applying the one or more electrical pulses to a concha of the ear.

8. The method of claim 1, wherein applying the one or more electrical pulses to the ear of the subject comprises applying the one or more electrical pulses to a tragus of the ear.

9. The method of claim 1, wherein applying the one or more electrical pulses to the ear of the subject comprises applying the one or more electrical pulses to an external ear of the subject.

10. The method of claim 1, further comprising: quantifying a baseline pupil diameter, wherein measuring, by the pupil measurement device, pupil diameter over time comprises measuring changes in pupil diameter from the baseline pupil diameter after activation of the neurotransmitter system.

11. The method of claim 1, wherein the one or more electrical pulses are sufficient to cause release of neurotransmitters.

12. The method of claim 11, wherein the neurotransmitters comprise norepinephrine, acetylcholine, gamma aminobutyric acid (GABA), or dopamine.

13. The method of claim 10, further comprising:
- selecting at least one stimulation parameter for applying the one or more electrical pulses to the ear;
- establishing a perceptual threshold; and
- adjusting the at least one stimulation parameter based on the perceptual threshold for applying the one or more electrical pulses to the ear.

14. The method of claim 13, wherein the at least one stimulation parameter comprises a current amplitude.

15. The method of claim 1, wherein measuring, by the pupil measurement device, pupil diameter over time comprises measuring, by the pupil measurement device, the increase in pupil diameter during application of the one or more electrical pulses.

16. The method of claim 1, wherein the pupil measurement device is integrated within a commercially available eye tracking system.

17. The method of claim 1, wherein the method is performed using a system comprising:
- a stimulation apparatus comprising first and second electrodes;
- a stimulation generator in electrical communication with the first and second electrodes;
- the pupil measurement device configured to measure pupil diameter; and
- the computing device in communication with the pupil measurement device, wherein the computing device is configured to receive measurements from the pupil measurement device,
- wherein applying one or more electrical pulses to the ear of the subject comprises:

positioning the first and second electrodes of the stimulation apparatus in contact with the ear of the subject; and generating, by the stimulation generator, current between the first and second electrodes.

18. The method of claim 17, wherein the stimulation apparatus comprises an elongated body having a longitudinal axis and first and second ends that are spaced along the longitudinal axis, wherein one or both of the first and second electrodes are positioned on the elongated body, and wherein at least a portion of the elongated body is receivable into an ear canal of the ear.

19. The method of claim 1, further comprising:

changing at least one of:

a position of the first electrode;

an amplitude of the one or more electrical pulses; or a frequency of the one or more electrical pulses; and applying one or more additional electrical pulses to the ear of the subject to stimulate the auricular branch of the vagus nerve of the subject.

20. The method of claim 1, wherein the behavior, environmental, or task-related event to be learned is to extinguish memories or conditioned fears.

* * * * *